(12) United States Patent
Moraitis

(10) Patent No.: US 11,327,083 B2
(45) Date of Patent: May 10, 2022

(54) TREATMENT AND DIFFERENTIAL DIAGNOSIS OF CUSHING'S DISEASE AND ECTOPIC CUSHING'S SYNDROME

(71) Applicant: Corcept Therapeutics, Inc., Menlo Park, CA (US)

(72) Inventor: Andreas G. Moraitis, Menlo Park, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 881 days.

(21) Appl. No.: 16/158,866

(22) Filed: Oct. 12, 2018

(65) Prior Publication Data
US 2019/0041409 A1 Feb. 7, 2019

Related U.S. Application Data

(63) Continuation of application No. 15/627,414, filed on Jun. 19, 2017, now Pat. No. 10,151,763, which is a
(Continued)

(51) Int. Cl.
*G01N 33/74* (2006.01)
*G16H 50/20* (2018.01)
(Continued)

(52) U.S. Cl.
CPC ......... *G01N 33/743* (2013.01); *A61B 5/4227* (2013.01); *G01N 33/74* (2013.01);
(Continued)

(58) Field of Classification Search
None
See application file for complete search history.

(56) References Cited

U.S. PATENT DOCUMENTS 9,295,680 B2 3/2016 Altschul et al.
9,333,234 B2 5/2016 Gericke et al.
(Continued)

FOREIGN PATENT DOCUMENTS

JP 2014510904 A 5/2014
JP 2015512923 A 4/2015
(Continued)

OTHER PUBLICATIONS

Boscaro et al. Approach to the Patient with Possible Cushing's Syndrome. J Clin Endocritnol Metab 2009, 94(9), pp. 3121-3131 (Year: 2009).*
(Continued)

*Primary Examiner* — Olivia M. Wise
(74) *Attorney, Agent, or Firm* — Kilpatrick Townsend & Stockton LLP

(57) ABSTRACT

Improved methods and systems for diagnosing and for treating Cushing's syndrome and Cushing's Disease are provided herein, including methods and systems for concurrently treating Cushing's syndrome and differentially diagnosing Cushing's Disease from Ectopic Cushing's Syndrome in a patient with an established diagnosis of ACTH-dependent Cushing's syndrome. Treatment methods can use glucocorticoid receptor antagonists (GRAs), which differentially affect the ratio of cortisol to ACTH levels in patients having Cushing's Disease versus patients having Ectopic Cushing's Syndrome. Methods for concurrently treating and differentially diagnosing Cushing's Disease from Ectopic Cushing's Syndrome include obtaining baseline cortisol and ACTH levels of a patient, treating the patient with a GRA according to a protocol that would typically substantially elevate cortisol levels, obtaining post-treatment cortisol and ACTH levels of the patient, determining a differential relationship between baseline cortisol and ACTH levels and post-treatment cortisol and ACTH levels and providing a positive diagnosis based on the differential relationship.

29 Claims, 5 Drawing Sheets

Related U.S. Application Data continuation-in-part of application No. PCT/US2017/013974, filed on Jan. 18, 2017.

(60) Provisional application No. 62/280,424, filed on Jan. 19, 2016.

(51) Int. Cl.
    *G16H 20/17*     (2018.01)
    *G16H 50/30*     (2018.01)
    *A61B 5/00*     (2006.01)

(52) U.S. Cl.
CPC .............. *G16H 20/17* (2018.01); *G16H 50/20* (2018.01); *G16H 50/30* (2018.01); *G01N 2333/575* (2013.01); *G01N 2333/723* (2013.01); *G01N 2800/04* (2013.01)

(56) References Cited

U.S. PATENT DOCUMENTS

| | | | |
|---|---|---|---|
| 10,151,763 | B2 | 12/2018 | Moraitis |
| 2004/0138516 | A1 | 7/2004 | Osorio et al. |
| 2014/0170768 | A1 | 6/2014 | Ehrenkranz |
| 2018/0011113 | A1 | 1/2018 | Moraitis |

FOREIGN PATENT DOCUMENTS

| | | | |
|---|---|---|---|
| JP | 2015159766 | A | 9/2015 |
| WO | 2004041215 | A2 | 5/2004 |
| WO | 2005070893 | A2 | 8/2005 |
| WO | 2005087769 | A1 | 9/2005 |
| WO | 2006014394 | A1 | 2/2006 |
| WO | 2008060391 | A2 | 5/2008 |
| WO | 2009050136 | A2 | 4/2009 |

OTHER PUBLICATIONS

Hur et al., "Clinical Guidelines for the Diagnosis and Treatment of Cushing's Disease in Korea", Endocrinology and Metabolism, vol. 30, No. 1, Mar. 27, 2015, pp. 7-18.
Raff et al., "Cushing's Syndrome: from Physiological Principles to Diagnosis and Clinical Care", The Journal of Physiology, vol. 593, No. 3, 2015, pp. 493-506.
SG11201806101S, "Written Opinion", Dec. 5, 2019, 9 pages.
Agarwal et al., "Glucocorticoid Antagonists", FEBS Letters, vol. 217, No. 2, Jun. 15, 1987, p. 221-226.
Albertson et al., "Effect of the antiglucocorticoid RU486 on adrenal steroidogenic enzyme activity and steroidogenesis," EP J. of Endrocrino. (1994) 130: 195-200.
Asser et al., "Autocrine positive regulatory feedback of glucocorticoid secretion: Glucocorticoid receptor directly impacts H295R human adrenocortical cell function," Mol. Cell. Endocrino. (2014) 395(1-2):1-9.
Benagiano et al., "Selective Progesterone Receptor Modulators 3: Use in Oncology, Endocrinology and Psychiatry", Expert Opin. Pharmacother, vol. 9, Issue 14, Oct. 2008, pp. 2487-2496.
Bertagna et al., "Pituitary-Adrenal Response to the Antiglucocorticoid Action of RU 486 in Cushing's Syndrome," J. Clin Endocrinol Metab (1986) 63:639-643.
Chrousos et al., "Glucocorticoids and glucocorticoid antagonists: Lessions from RU 486," Kidney International, vol. 34, Suppl. 26 (1988), pp. S-18-S-23.
Chu et al., "Successful Long-Term Treatment of Refractory Cushing's Disease with High-Dose Mifepristone (RU 486)", J. Clin Endocrinology Metab, vol. 86, No. 8, Aug. 2001, pp. 3568-3573.
Cuneo et al., "Metyrapone pre-treated inferior petrosal sinus sampling in the differential diagnosis of ACTH-dependent Cushing's syndrome," Clinical Endocrinology (1997) 46:607-618.
Ehrenkranz et al. "SUN-66: Using Mifepristone to Differentiate Cushing's Disease from Cushing's Syndrome," The Endocrine Society's 95th Annual Meeting and Expo, Jun. 15-18, 2013 (San Francisco) Abstract.
El-Shafie et al., "Adrenocorticotropic Hormone-Dependent Cushing's Syndrome :Use of an octreotide trial to distinguish between pituitary or ectopic sources", Sultan Qaboos University Medical Journal, vol. 15, Issue 1, Jan. 21, 2015, pp. 120-123.
Fein et al., "Sustained weight loss in patients treated with mifepristone for Cushing's syndrome: a follow-up analysis of the SEISMIC study and long-term extension", BMC Endocr Disord. vol. 15, Issue 63, 2015, pp. 1-7.
Fleseriu et al., "Mifepristone, a Glucocorticoid Receptor Antagonist, Produces Clinical and Metabolic Benefits in Patients with Cushing's Syndrome", The Journal of Clinical Endocrinology & Metabolism, vol. 97, Issue 6, Jun. 2012, pp. 2039-2049.
Gross et al., "Mifepristone Reduces Weight Gain and Improves Metabolic Abnormalities Associated With Risperidone Treatment in Normal Men", Obesity vol. 18, No. 12, Dec. 2010, pp. 2295-2300.
Healy et al., "Pituitary and adrenal responses to the anti-progesterone and anti-glucocorticoid steroid RU486 in primates," J. Clin Endocrinol Metab (1983) 57(4):863-865.
Lee et al., "Office of Clinical Pharmacology Review", NDA 20687 (Addendum, Korlyn™, Mifepristone), 2012, pp. 1-119.
"Medical Encyclopedia of Medline", Available on Internet at: http://www.nlm.nih.gov/medlineplus/ency/articie/003430.htm, Oct. 2005, 4 pages.
Moncet et al., "Ketoconazole therapy: an efficacious alternative to achieve eucortisolism in patients with Cushing's syndrome", Medicina 67, 2007, pp. 26-31.
PCT/EP2008/063699, "International Search Report", dated May 6, 2009, pp. 2-6.
PCT/US2017/013974, "International Search Report and Written Opinion", dated Apr. 20, 2017, 12 pages.
Reimondo et al., "The corticotrophin-releasing hormone test is the most reliable noninvasive method to differentiate pituitary from ectopic ACTH secretion in Cushing's syndrome", Clinical Endocrinology, vol. 58,, 2003, pp. 718-724.
Ritzel et al., "ACTH after 15 min distinguishes between Cushing's disease and ectopic Cushing's syndrome: a proposal fora short and simple CRH test", European Journal of Endocrinology, vol. 173, No. 2,, 2015, pp. 197-204.
Sarkar, "Mifepristone: bioavailability, pharmacokinetics and use-effectiveness", European Journal of Obstetrics and Gynecology and Reproductive Biology, vol. 101, 2002, pp. 113-120.
Tritos et al., "Management of Cushing Disease", Nature Reviews Endocrinology, vol. 7, Feb. 8, 2011, pp. 279-289.
Tsigos, "Differential Diagnosis and Management of Cushing's Syndrome", Ann. Rev. Med., vol. 47, 1996, pp. 443-461.
Van Der et al., "Rapid reversal of acute psychosis in the cushing syndrome with the cortisol-receptor antagonist mifepristone (RU486)", Annals of Internal Medicine, vol. 114, No. 2, Jan. 15, 1991, pp. 143-144.
Verhelst et al., "Short and long-term responses to metyrapone in the medical management of 91 patients with Cushing's syndrome", Clinical Endocrinology, vol. 35, 1991, pp. 169-178.
Diez et al., "Pharmacological Therapy of Cushing's Syndrome: Drugs and Indications," Mini Reviews in Medicinal Chemistry, vol. 7, No. 5, 2007, pp. 467-480.
Raff, "Cushing Syndrome Update On Testing," Endocrinology and Metabolism Clinics of North America, vol. 44, No. 1, Feb. 28, 2015, pp. 43-50.
EP17741860.5, "Extended European Search Report", dated Jun. 21, 2019, 7 pages.
PCT/US2017/013974, "International Preliminary Report on Patentability", dated Aug. 2, 2018, 8 pages.

\* cited by examiner

TREATMENT AND DIFFERENTIAL DIAGNOSIS OF CUSHING'S DISEASE AND ECTOPIC CUSHING'S SYNDROME

CROSS-REFERENCES TO RELATED APPLICATIONS

This application is a Continuation of U.S. application Ser. No. 15/627,414, filed Jun. 19, 2017, which is a US National Phase Continuation-in-Part Application of PCT/US2017/13974, filed Jan. 18, 2017, which claims the benefit of U.S. Provisional Application No. 62/280,424, filed Jan. 19, 2016, the entire contents of each application of which is hereby incorporated by reference.

BACKGROUND

Cortisol is a steroid produced by the adrenal glands and is used in the body to respond to physical and emotional stress and to maintain adequate energy supply and blood sugar levels. Cortisol production is highly regulated by the hypothalamic-pituitary-adrenal axis (HPA) through a complex set of direct influences and negative feedback interactions. In healthy individuals, insufficient cortisol in the bloodstream triggers the hypothalamus to release corticotropin-releasing hormone (CRH) which signals to the pituitary gland to release adrenocorticotropic hormone (ACTH), which in turn stimulates the adrenal glands to produce more cortisol. Excessive cortisol inhibits hypothalamus from producing CRH, thus inhibiting the pituitary gland from releasing ACTH, which in turn suppresses cortisol production. Excessive cortisol inhibits also the corticotroph pituitary cells from producing ACTH, thus inhibiting the adrenal glands from producing cortisol. The HPA regulation also results in a diurnal rhythm of cortisol levels, reaching peaks in the morning and nadirs around midnight. Pathological conditions associated with the HPA can affect the diurnal rhythm of the cortisol and ACTH production and cause serious health problems.

Cushing's Syndrome is one of these problems. Patients having Cushing's Syndrome usually have easy bruising; abdominal obesity and thin arms and legs; facial plethora; acne; proximal muscle weakness; and/or red purple stripes across the body. Cushing's Syndrome is accompanied by hypercortisolemia, a condition involving a prolonged excess of circulating cortisol. Cushing's Syndrome can be classified as exogenous Cushing's Syndrome, which is caused by excess use of glucocorticoids drugs, such as prednisone, dexamethasone, and hydrocortisone, and endogenous Cushing's Syndrome, which is caused by deregulatory abnormalities in the HPA axis. Endogenous Cushing's Syndrome consists of the ACTH-independent Cushing's Syndrome, characterized by an overproduction of cortisol in the absence of elevation of ACTH secretion and the ACTH-dependent Cushing's Syndrome, characterized by excessive ACTH secretion. Cushing's syndrome is often accompanied by hyperglycemia, a symptom of diabetes, and such hyperglycemia is secondary to hypercortisolemia.

ACTH-dependent Cushing's Syndrome includes roughly 80% of patients having endogenous Cushing's Syndrome and consists of two major forms: Cushing's Disease and Ectopic Cushing's Syndrome. The former is caused by a pituitary tumor and the latter is caused by a tumor outside the pituitary. Correct differential diagnosis between the Cushing Disease and Ectopic Cushing's Syndrome is important for endocrinologists to recommend transphenoidal surgery or appropriate imaging to identify source of the ectopic ACTH secretion.

Current approaches of differentially diagnosing patients with ACTH-dependent Cushing's Syndrome involve measuring ACTH levels from samples obtained from both inferior petrosal venous sinus (IPS)—a procedure referred to as inferior petrosal venous sinus sampling (IPSS)—and from the internal jugular or another peripheral vein from the patient. Some of these approaches require collecting blood samples both before and after administration of an agent, such as CRH, DDAVP, or metyrapone. ACTH concentration in the samples are measured and a central to periphery ACTH ratio is determined and compared with a predetermined threshold to determine whether the patient has Cushing's Disease or Ectopic Cushing's Syndrome. Generally, a central-to-periphery ACTH ratio of >2 before and >3 after the administration of CRH or DDAVP is consistent with Cushing Disease while a lower ratio favors Ectopic Cushing's Syndrome. These procedures require not only prolonged catheterization with the likelihood of infection, thrombosis, or bleeding rising with the duration of catheterization, but also sophisticated handling that can only be conducted by trained professionals, e.g., an interventional radiologist. Abnormal venous drainage of the pituitary could lead to false negative IPSS results that could delay transphenoidal surgery, lead to unnecessary imaging studies and possibly unnecessary bilateral adrenalectomy. In addition, CRH is expensive to produce and metyrapone is currently not available in the United States. These current diagnosis methods thus have serious limitations.

SUMMARY

In one aspect, provided herein is a method of differentially diagnosing Cushing's Disease from Ectopic Cushing's Syndrome in a patient with an established diagnosis of ACTH-dependent Cushing's Syndrome. The method comprises: (i) determining a baseline cortisol level and a baseline adrenocorticotropic hormone (ACTH) level from one or more pretreatment samples taken from the patient; (ii) administering a glucocorticoid receptor antagonist (GRA) to the patient for a period of not less than 5 weeks and in an amount effective to raise ACTH and cortisol levels in a healthy individual by at least two fold; (iii) determining a second ACTH level and a second cortisol level from one or more second samples taken from the patient in step (ii); (iv) calculating a baseline ratio of cortisol to ACTH ("baseline C:A ratio") using the baseline levels of cortisol and ACTH, and calculating a GRA-exposed ratio of cortisol to ACTH ("GRA-exposed C:A ratio") using the second cortisol and ACTH levels; and, (v) diagnosing the patient as having Ectopic Cushing's Syndrome if the GRA-exposed C:A ratio of cortisol to ACTH has decreased by greater than 50% compared to the baseline C:A ratio, or diagnosing the patient as having Cushing's Disease if the GRA-exposed C:A ratio has increased by greater than 50% compared to the baseline C:A ratio.

In some embodiments, the GRA is a non-steroidal GRA. In some embodiments, GRA is mifepristone. In some embodiments, the GRA is selected from the group consisting of (R)-4a-(ethoxymethyl)-1-(4-fluorophenyl)-6-((4-(trifluoromethyl)phenyl)sulfonyl)-4,4a,5,6,7,8-hexahydro-1H-pyrazolo[3,4-g]isoquinoline;

6-((1r,4r)-4-phenylcyclohexyl)-5-(3-(trifluoromethyl)benzyl)pyrimidine-2,4(1H,3H)-dione;

(R)-(1-(4-fluorophenyl)-6-((4-(trifluoromethyl)phenyl)
   sulfonyl)-4,4a,5,6,7,8-hexahydro-1H-pyrazolo[3,4-g]
   isoquinolin-4a-yl)(thiazol-2-yl)methanone;
(R)-(1-(4-fluorophenyl)-6-((1-methyl-1H-pyrazol-4-yl)
   sulfonyl)-4,4a,5,6,7,8-hexahydro-1H-pyrazolo[3,4-g]
   isoquinolin-4a-yl)(4-(trifluoromethyl)pyridin-2-yl)
   methanone; and
((4aR,8aS)-1-(4-fluorophenyl)-6-((2-methyl-2H-1,2,3-
   triazol-4-yl)sulfonyl)-4,4a,5,6,7,8,8a,9-octahydro-1H-
   pyrazolo[3,4-g]isoquinolin-4a-yl)(4-(trifluoromethyl)
   pyridin-2-yl)methanone.

In some embodiments the one or more second samples are taken from the patients after mifepristone has been administered for a minimum of 6 weeks, e.g., between 6 and 10 weeks, or between 10 and 24 weeks; and/or mifepristone is administered on a daily basis and is equal to 5-20 mg/kg of the patient.

In some embodiments, the pretreatment samples and second samples are from saliva. In some embodiments, the pretreatment samples and second samples are from plasma and measured in µg/dl. In some embodiments, the pretreatment samples and second samples are from 24-hour urine collections.

In another aspect, provided herein is a system configured for facilitating differential diagnosis between Ectopic Cushing's Syndrome and Cushing's Disease in a patient with an established diagnosis of ACTH-dependent Cushing's Syndrome. Such systems can encompass a computing system having a diagnostic module that includes a processor coupled with a memory via an interconnect, a communications module or input and an output module. It is appreciated that the interconnect can include an interconnect bus or can include any communication coupling, including wireless couplings and remotely access through a network, the internet or a cloud server. The memory can include a tangible, non-transitory storage medium having instructions recorded thereon for causing the processor to compare a first set of values corresponding to baseline levels of cortisol and ACTH in the patient before exposure to a GRA and a second set of values corresponding to exposed-GRA levels of cortisol and ACTH in the patient after a treatment with GRA. Typically, the GRA treatment is administration of a GRA for a minimum of 5 weeks amount effective to raise ACTH and cortisol levels in a health individual by at least two fold. The system is then configured to determine a differential relationship between the first and second set of values or associated ratios and output the differential relationship and/or a positive diagnosis of Ectopic Cushing's Syndrome or Cushing's Disease to a user.

In another aspect, methods of differentially diagnosing Cushing's Disease from Ectopic Cushing's Syndrome in a patient with an established diagnosis of ACTH-dependent Cushing's Syndrome are provided herein. Such methods can be facilitated by use of any of the systems described herein, or similar such systems. An example of such a method includes a step of obtaining, with a computing device associated with a treating physician, a first set of values and a second set of values. The first set of values represent a baseline cortisol level and a baseline ACTH level or a baseline ratio between the baseline cortisol and ACTH levels and correspond to one or more pre-treatment samples from the patient. The second set of values represent an exposed-GRA cortisol level and an exposed-GRA ACTH level or a ratio between the exposed-GRA cortisol and ACTH levels corresponding to one or more post-treatment samples from the patient obtained after undergoing a GRA treatment according to a predetermined protocol. The methods can be designated as corresponding to baseline or post-treatment samples within a memory of the computing device. The ratio between a cortisol level and an ACTH level may be determined, termed herein a "C:A ratio". A baseline C:A ratio may be determined from levels measured prior to GRA treatment, and a GRA-exposed C:A level may be determined from levels measured during or following GRA treatment. The method further includes determining, with the computing device, a differential relationship between the first and second set of values and then outputting to a user an indication of the differential diagnosis. If the differential relationship represents a decrease of the ratio calculated from exposed-GRA level of cortisol divided by the exposed-GRA level of ACTH that is greater than a pre-determined decrease (e.g. the C:A ratio calculated from exposed-GRA levels is less than 50% of baseline C:A ratio calculated from baseline cortisol and ACTH levels), the differential relationship indicates a positive diagnosis for Ectopic Cushing's Syndrome. If the differential relationship represents a pre-determined increase (e.g. an increase of greater than 50% of baseline ratio) of the exposed-GRA levels (e.g., the ratio calculated from exposed-GRA level of cortisol divided by the exposed-GRA level of ACTH that is greater than the baseline C:A ratio by at least 50% of the baseline C:A ratio calculated from baseline cortisol and ACTH levels), the differential relationship indicates a positive diagnosis for Cushing's Disease. The output can be displayed on a user interface display of the computing device or can be output to an external computing device for display or printing to a user.

In one aspect, the systems are configured to automatically perform the diagnosis methods described herein when baseline and post-treatment samples are obtained from a patient with an established diagnosis of ACTH-dependent Cushing's Syndrome. In another aspect, the system is configured to perform the diagnostic methods described herein upon receiving a request for such a diagnosis from a treating physician or associated personnel.

In another aspect, provided herein is a method of concurrently treating Cushing's Syndrome and differentially diagnosing Cushing's Disease from Ectopic Cushing's Syndrome in a patient with an established diagnosis of ACTH-dependent Cushing's Syndrome. The method comprises: (i) determining a baseline cortisol level and a baseline adrenocorticotropic hormone (ACTH) level from one or more pretreatment samples taken from the patient; (ii) administering a glucocorticoid receptor antagonist (GRA) effective to treat Cushing's Syndrome in the patient, thereby treating Cushing's Syndrome; (iii) continuing said treatment of Cushing's Syndrome by administering said GRA to the patient for a period of not less than 5 weeks and in an amount effective to raise ACTH and cortisol levels in a healthy individual by at least two fold; (iv) determining a second ACTH level and a second cortisol level from one or more second samples taken from the patient in step (iii); (v) calculating a baseline ratio of cortisol to ACTH ("baseline C:A ratio") using the baseline levels of cortisol and ACTH, and calculating a GRA-exposed ratio of cortisol to ACTH ("GRA-exposed C:A ratio") using the second cortisol and ACTH levels; and, (vi) diagnosing the patient as having Ectopic Cushing's Syndrome if the GRA-exposed C:A ratio of cortisol to ACTH has decreased by greater than 50% compared to the baseline C:A ratio, or diagnosing the patient as having Cushing's Disease if the GRA-exposed C:A ratio has increased by greater than 50% compared to the baseline C:A ratio.

In another aspect, provided herein is a method of concurrently 1) controlling hyperglycemia secondary to hypercortisolemia in a patient suffering from endogenous ACTH-dependent Cushing's syndrome and 2) differentially diagnosing Cushing's Disease from Ectopic Cushing's Syndrome in the patient. The method comprises: (i) taking one or more pretreatment samples from the patient in order to determine a baseline cortisol level and a baseline adrenocorticotropic hormone (ACTH) level; (ii) administering a glucocorticoid receptor antagonist (GRA) to the patient; (iii) continuing said treatment by administering said GRA to the patient for a period of not less than 5 weeks; (iv) taking one or more GRA-exposed samples from said patient in order to determine a GRA-exposed ACTH level and a GRA-exposed cortisol level; (v) calculating a baseline ratio of cortisol to ACTH ("baseline C:A ratio") using the baseline levels of cortisol and ACTH, and calculating a GRA-exposed ratio of cortisol to ACTH ("GRA-exposed C:A ratio") using the GRA-exposed cortisol level and the GRA-exposed ACTH level; and, (vi) diagnosing the patient as having Ectopic Cushing's Syndrome if the GRA-exposed C:A ratio is lower than the baseline C:A ratio by at least 50% of the baseline C:A ratio, or diagnosing the patient as a having Cushing's Disease if the GRA-exposed C:A ratio is higher than the baseline C:A ratio by more than 20% of the baseline C:A ratio. In embodiments, the GRA administration is effective to control hyperglycemia secondary to hypercortisolemia in the patient. In embodiments, the GRA is administered in an amount effective to raise ACTH and cortisol levels in a healthy individual by at least two fold. In embodiments, the GRA is mifepristone. In embodiments, the GRA is a non-steroidal GRA.

In yet another aspect, methods of concurrently treating Cushing's Syndrome and differentially diagnosing Cushing's Disease from Ectopic Cushing's Syndrome in a patient with an established diagnosis of ACTH-dependent Cushing's Syndrome are provided herein. Such methods can be facilitated by use of any of the systems described herein, or similar such systems. An example of such a method includes a step of obtaining, with a computing device associated with a treating physician, a first set of values; then administering a glucocorticoid receptor antagonist (GRA) effective to treat Cushing's Syndrome in the patient, thereby treating Cushing's Syndrome; and then obtaining, with a computing device associated with a treating physician, a second set of values. The first set of values represent a baseline cortisol level and a baseline ACTH level or a baseline ratio between the baseline cortisol and ACTH levels and correspond to one or more pre-treatment samples from the patient. The second set of values represent an exposed-GRA cortisol level and an exposed-GRA ACTH level or a ratio between the exposed-GRA cortisol and ACTH levels corresponding to one or more post-treatment samples from the patient obtained after undergoing a GRA treatment according to a predetermined protocol. The predetermined protocol may comprise one, two, or more administrations of a GRA to treat Cushing's Syndrome in the patient. The methods can be designated as corresponding to baseline or post-treatment samples within a memory of the computing device. The method further includes determining, with the computing device, a differential relationship between the first and second set of values and then outputting to a user an indication of the differential diagnosis. If the differential relationship represents a pre-determined decrease (e.g. greater than 50% of baseline ratio) of the exposed-GRA levels (e.g. ratio), the indication represents a positive diagnosis for Ectopic Cushing's Syndrome. If the differential relationship represents a pre-determined increase (e.g. greater than 50% of baseline ratio) of the exposed-GRA levels (e.g., ratio), the indication a positive diagnosis for Cushing's Disease. The output can be displayed on a user interface display of the computing device or can be output to an external computing device for display or printing to a user.

In yet another aspect, methods of concurrently controlling hyperglycemia secondary to hypercortisolemia in a patient suffering from endogenous ACTH-dependent Cushing's syndrome and differentially diagnosing Cushing's Disease from Ectopic Cushing's Syndrome in the patient are provided herein. Such methods can be facilitated by use of any of the systems described herein, or similar such systems. For example, Applicant discloses herein a method of concurrently 1) controlling hyperglycemia secondary to hypercortisolemia in a patient suffering from endogenous ACTH-dependent Cushing's syndrome and 2) differentially diagnosing Cushing's Disease from Ectopic Cushing's Syndrome in said patient, the method comprising: taking one or more pretreatment samples from said patient in order to determine a baseline cortisol level and a baseline adrenocorticotropic hormone (ACTH) level; obtaining, with a computing system associated with a treating physician, a first set of values representing said baseline cortisol level and said baseline ACTH level, or a baseline C:A ratio between the baseline cortisol and ACTH levels determined from said one or more pre-treatment samples from the patient; then administering a glucocorticoid receptor antagonist (GRA) to the patient; then taking one or more GRA-exposed samples from said patient in order to determine a GRA-exposed cortisol level and a GRA-exposed ACTH level; obtaining, with the computing system, a second set of values representing said GRA-exposed cortisol level and said GRA-exposed ACTH level or a GRA-exposed ratio between the GRA-exposed cortisol and GRA-exposed ACTH levels corresponding to one or more GRA-exposed samples obtained from the patient after GRA administration; determining, with the computing system, a differential relationship between the first and second set of values; and outputting to a user, with the computing system, an indication representing a positive diagnosis for Ectopic Cushing's Syndrome, if the differential relationship represents or exceeds a pre-determined decrease of the GRA-exposed levels as compared to the baseline levels; and outputting to a user, with the computing system, an indication representing a positive diagnosis for Cushing's Disease, if the differential relationship represents or exceeds a pre-determined increase of the GRA-exposed levels as compared to the baseline levels. In embodiments of such methods, the pre-determined decrease may be, e.g., 50%, and an indication representing a positive diagnosis for Ectopic Cushing's Syndrome may then be output if the GRA-exposed C:A ratio is lower than the baseline C:A ratio by at least 50% of the baseline C:A ratio, wherein said GRA-exposed C:A ratio is a ratio between the GRA-exposed cortisol and GRA-exposed ACTH levels corresponding to one or more GRA-exposed samples from the patient obtained after GRA administration. In embodiments of such methods, where the pre-determined increase may be, e.g., 20%, and an indication representing a positive diagnosis for Cushing's Disease may then output if the GRA-exposed C:A ratio is higher than the baseline C:A ratio by at least 20% of the baseline C:A ratio, wherein said GRA-exposed C:A ratio is a ratio between the GRA-exposed cortisol and GRA-exposed ACTH levels corresponding to one or more GRA-exposed samples from the patient obtained after GRA administration. In embodiments of such methods, the pre-determined decrease is 50% and the pre-determined increase is 20% of the baseline C:A ratio. In embodiments of such methods, the pre-determined treatment protocol may include administration of the GRA to the patient for a minimum of five weeks. In embodiments, the GRA is mifepristone, and said mifepristone is administered on a daily basis at a dosage that does not exceed 20 mg/kg of the patient. In embodiments of such methods, obtaining the baseline C:A ratio may comprise receiving, with the computing system, each of a baseline cortisol level and a baseline ACTH level and determining the baseline ratio therefrom. In embodiments of such methods, obtaining the first set of values may comprise storing, in a memory of the computing system, the first set of values designated as corresponding to baseline levels of the patient and obtaining the second set of values may comprise storing the second set of values, in the memory, designated as corresponding to GRA-exposed levels of the patient. In embodiments of such methods, obtaining the first and second sets of values may comprise accessing the first and second sets of values remotely through a server of a medical facility or laboratory associated with the patient. In embodiments, the GRA administration is effective to control hyperglycemia secondary to hypercortisolemia in the patient. In embodiments, the GRA is administered in an amount effective to raise ACTH and cortisol levels in a healthy individual by at least two fold. In embodiments, the GRA is mifepristone. In embodiments, the GRA is a non-steroidal GRA.

DETAILED DESCRIPTION

I. Introduction

Figure 1:
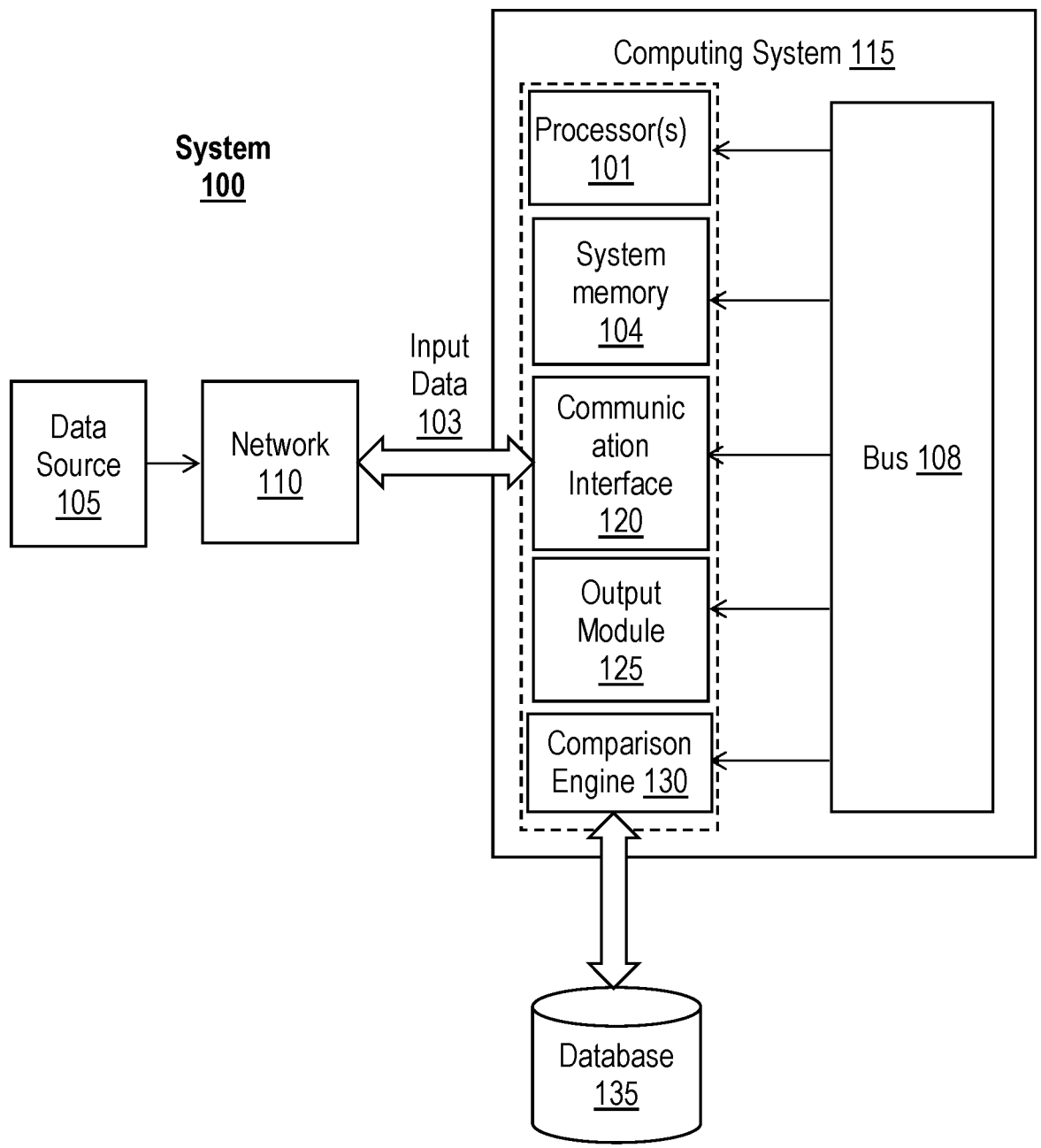
FIG. 1 shows a system adapted for differentially diagnosing Cushing's Disease from Ectopic Cushing's Syndrome in a patient with an established diagnosis of ACTH-dependent Cushing's Syndrome in accordance with various embodiments.

This invention involves the use of glucocorticoid receptor antagonists (GRAs) to provide a robust and convenient means to alter ACTH and cortisol production and/or secretion for the purpose of differentially diagnosing patients having ACTH-dependent Cushing's Syndrome—where the differential diagnosis is between Cushing's Disease and Ectopic Cushing's Syndrome. Samples are taken before and after GRA has been administered for a sufficient period of time. Cortisol and ACTH levels of the samples are assessed and the ratios of the two hormones before and after the GRA treatment are compared to determine which form of ACTH-dependent Cushing's Syndrome the patient has.

The claimed disclosed herein thus dispense the need for complicated, invasive IPSS procedures as described above and can be performed based on patient samples obtained during routine physical examinations. The diagnosis is therefore more accurate, convenient, and affordable as compared to the existing methods.

II. Definitions

The term "endogenous Cushing's Syndrome" refers to a form of Cushing's Syndrome, where the excess cortisol level (hypercortisolemia) results from the body's own overproduction of cortisol. The hypercortisolemia of endogenous Cushing's syndrome often results in hyperglycemia secondary to hypercortisolemia.

The term "Adrenocorticotropic hormone (ACTH)-dependent Cushing's Syndrome" refers to a form of endogenous Cushing's Syndrome, which is caused by abnormal production of ACTH. There are two major forms of ACTH-dependent Cushing's Syndrome: Cushing Disease (accounting for about 80% of the cases) and Ectopic Cushing's Syndrome (accounting for 20% of the cases).

The term "cortisol to ACTH ratio" or "C:A ratio" refers a ratio derived from the numerical values using appropriate scientific notation where the ratios are calculated using the coefficient value of the cortisol level over the coefficient value of the ACTH level with the exponents and base numbers remaining the same as from the baseline sample. The exponents and base values are not a part of the ratio. Accordingly, if the cortisol baseline level is $10 \times 10^{-6}$ grams/dl and the ACTH baseline level is $5 \times 10^{-12}$ grams/ml plasma, then for purposes of this invention, the ratio is 10:5 or 2.0. If, after the treatment with GRA, the cortisol level is $4 \times 10^{-6}$ grams/dl and ACTH level is $5 \times 10^{-12}$ grams/ml plasma, then the post-treatment ratio, a.k.a., GRA exposed ratio, is 4:5 or 0.8. This decrease in the C:A ratio would predict that the patient who has an established diagnosis of ACTH-dependent Cushing's Syndrome has one or more ectopic tumors.

The term "pretreatment sample" refers to a sample obtained from the patient before administration of a GRA.

The term "second sample" refers to a sample obtained from the patient at the end of a period during which the patient has been treated with GRA.

The term "baseline cortisol level" and the term "baseline ACTH level" refer to the amount, level, or concentration of cortisol and ACTH, respectively, in a patient before the GRA treatment. Baseline cortisol or ACTH level is determined by assessing the cortisol or ACTH level in a pretreatment sample.

The term "second cortisol level" and the term "second ACTH level" refer the amount, level, or concentration of cortisol and ACTH, respectively, in a patient after a period of GRA treatment. Second cortisol or ACTH level is determined by assessing the cortisol or ACTH level in a second sample.

The term "baseline ratio of cortisol to ACTH" or "baseline C:A ratio" disclosed herein refers to the ratio of cortisol to ACTH levels in a patient before GRA treatment. Baseline C:A ratio is determined by assessing the cortisol and ACTH levels in one or more pretreatment samples as indicated in the definition of the terms "cortisol to ACTH ratio" and "C:A ratio". Thus, the baseline C:A ratio is calculated using the coefficient value of the baseline cortisol level over the coefficient value of the baseline ACTH level with the exponents and base numbers remaining the same as from the baseline sample. The exponents and base values are not a part of the ratio.

The term "GRA-exposed ratio of cortisol to ACTH" or "GRA-exposed C:A ratio" disclosed herein refers to the ratio of cortisol to ACTH levels in a patient after a period of GRA treatment. GRA-exposed C:A ratio is determined by assessing the cortisol and ACTH levels in one or more second samples as indicated in the definition of the terms "cortisol to ACTH ratio" and "C:A ratio". Thus, the GRA-exposed C:A ratio is calculated using the coefficient value of the GRA-exposed cortisol level over the coefficient value of the GRA-exposed ACTH level with the exponents and base numbers remaining the same as from the baseline sample. The exponents and base values are not a part of the ratio.

The term "differentially diagnosing" refers to the distinguishing of a particular disease or condition from others that present similar symptoms. A differential diagnostic method is a systematic diagnostic method used to identify the presence of a condition where multiple alternatives are possible. This method is essentially a process of elimination or a process of obtaining information that shrinks the "probabilities" of candidate conditions to negligible levels.

The method uses evidence such as symptoms, test results, patient history, and medical knowledge to adjust epistemic confidences in the mind of the diagnostician (or, for computerized or computer-assisted diagnosis, the software of the system). Often each individual option of a possible disease is called a differential diagnosis.

The term "Ectopic Cushing's Syndrome" refers to the abnormal production of ACTH due to ectopic ACTH secretion by an extrapituitary tumor. Extrapituitary tumors frequently originate in lungs, the thymus, pancreas, adrenal gland, or thyroid.

The term "Cushing's Disease" refers to the condition in which the pituitary gland releases too much ACTH as a result of a tumor located in—or excess growth (hyperplasia) of—the pituitary gland. Cushing's Disease is a form of Cushing's Syndrome.

The term "hypercortisolemia" refers a condition of having a higher than normal amount of circulating cortisol. Hypercortisolemia often results in hyperglycemia secondary to hypercortisolemia.

The term "patient", "individual", or "subject" is used interchangeably to refer to a human subject. In some cases, the individual is one who has been diagnosed with ACTH-dependent Cushing's Syndrome. The term "healthy individual" refers to an individual who has normal HPA function.

The term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, epicutaneous, subcutaneous, intraperitoneal, intraventricular, and intracranial. Other modes of delivery include, but are not limited to, the use of liposomal formulations, intravenous infusion, and transdermal patches.

The term "sample" refers to a biological sample obtained from a human subject. The sample can be any cell, tissue or fluid from a human subject. Samples can be subject to various treatment, storage or processing procedures before being analyzed according to the methods described herein. Generally, the terms "sample" or "samples" are not intended to be limited by their source, origin, manner of procurement, treatment, processing, storage or analysis, or any modification.

The term "24-hour urine collection" refers a collection of all the urine a patient passes in a 24-hour period. During this 24-hour period, the patient is subject to certain dietary and other restrictions, as imposed by a medical professional. Examples of restrictions can be found at the Mayo Medical Laboratories web-site, file mc5343-23. A 24-hour urine collection is often ordered by a physician for a patient suspected of having Cushing's Syndrome.

The term "cortisol" refers to a glucocorticoid hormone that is produced by the zona fasciculata of the adrenal gland.

The term "adrenocorticotropic hormone" or "ACTH" refers to a polypeptide-based hormone that is normally produced and secreted by the anterior pituitary gland. ACTH stimulates secretion of cortisol and other glucocorticoids (GCs) by specialized cells of the adrenal cortex. In healthy mammals, ACTH secretion is tightly regulated. ACTH secretion is positively regulated by corticotropin releasing hormone (CRH), which is released by the hypothalamus. ACTH secretion is negatively regulated by cortisol and other glucocorticoids.

The term "measuring the level" in the context of cortisol, ACTH, or other steroids, refers determining, detecting, or quantitating the amount, level, or concentration of, for example, cortisol, ACTH or other steroids in a sample obtained from a subject.

The term a "increase" or a "decrease" refers to a detectable positive or negative change in quantity from a comparison control, e.g., an established standard control (such as an average level of cortisol in a normal, healthy subject who does not have hypercortisolemia). An increase is a positive change that is typically at least 5%, at least 10%, or at least 20%, or 50%, or 100%, and can be as high as at least 1.5-fold, at least 2-fold, at least 5-fold, or even 10-fold of the control value. Similarly, a decrease is a negative change that is typically at least 5%, at least 10%, or at least 20%, 30%, or 50%, or even as high as at least 80% or 90% of the control value. Other terms indicating quantitative changes or differences from a comparative basis, such as "more," "less," 'higher," and "lower," are used in this application in the same fashion as described above.

The term "normal reference value", "reference value", or "standard control level" refers to the a predetermined amount, level, or concentration of a particular analyte, e.g., ACTH, cortisol, or prolactin—by comparison to which a diagnosis of the presence or absence of a particular condition can be made, e.g., hypercortisolemia. Normal reference values referred to in this disclosure are in some cases provided by the commercial test that is used to determine the analyte levels. In some cases, a normal reference value, reference value, or standard control level is established as the average of the amount, level, or concentration of an analyte from one or more normal, healthy subjects, e.g., subjects who have normal HPA function. In some cases, they are established as a range of the level, amount, or concentration of the analyte in a group of healthy subjects. Normal reference values may vary depending on the nature of the sample, the manner or timing of sample collection, as well as other factors such as the sex, age, and ethnicity of the subjects for whom such a control value is established.

The term "elevated level", "elevated amount", or "elevated concentration" refers to the level or amount of the analyte that is higher than the normal reference value for that analyte.

The term "glucocorticosteroid" ("GC") or "glucocorticoid" refers to a steroid hormone that binds to a glucocorticoid receptor. Glucocorticosteroids are typically characterized by having 21 carbon atoms, an $\alpha,\beta$-unsaturated ketone in ring A, and an $\alpha$-ketol group attached to ring D. They differ in the extent of oxygenation or hydroxylation at C-11, C-17, and C-19; see Rawn, "Biosynthesis and Transport of Membrane Lipids and Formation of Cholesterol Derivatives," in Biochemistry, Daisy et al. (eds.), 1989, pg. 567.

The term "glucocorticoid receptor" ("GR") refers to the type II GR which specifically binds to cortisol and/or cortisol analogs such as dexamethasone; See, e.g., Turner & Muller, *J Mol. Endocrinol.*, 2005 (35): 283-292. The GR is also referred to as the cortisol receptor. The term includes isoforms of GR, recombinant GR and mutated GR. Inhibition constants ($K_i$) against the human GR receptor type II (Genbank: P04150) are between 0.0001 nM and 1,000 nM; preferably between 0.0005 nM and 10 nM, and most preferably between 0.001 nM and 1 nM.

The term "glucocorticoid receptor antagonist" or "GRA" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," the drug preferentially binds to the GR rather than to other nuclear receptors, such as the mineralocorticoid receptor (MR), androgen receptor (AR), or progesterone receptor (PR). It is preferred that the specific glucocorticoid receptor antagonist binds GR with an affinity that is 10× greater ($\frac{1}{10}^{th}$ the $K_d$ value) than its affinity to the MR, AR, or PR, both the MR and PR, both the MR and AR, both the AR and PR, or to the MR, AR, and PR. In a more preferred embodiment, the specific glucocorticoid receptor antagonist binds a GR with an affinity that is 100× greater ($\frac{1}{100}^{th}$ the $K_d$ value) than its affinity to the MR, AR, or PR, both the MR and PR, both the MR and AR, both the AR and PR, or to the MR, AR, and PR.

The term "selective inhibitor" in the context of a glucocorticoid receptor refers to a chemical compound that selectively interferes with the binding of a specific glucocorticoid receptor agonist and a glucocorticoid receptor.

The term "steroidal backbone" in the context of glucocorticoid receptor antagonists containing such refers to glucocorticoid receptor antagonists that contain modifications of the basic structure of cortisol, an endogenous steroidal glucocorticoid receptor ligand. The basic structure of a steroidal backbone is provided as Formula I:

Formula I

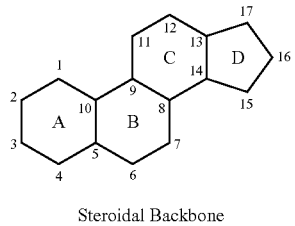

Steroidal Backbone

The two most commonly known classes of structural modifications of the cortisol steroid backbone to create glucocorticoid antagonists include modifications of the 11-β hydroxy group and modification of the 17-β side chain (See, e.g., Lefebvre (1989) J. Steroid Biochem. 33: 557-563).

As used herein, the term "non-steroidal backbone" in the context of glucocorticoid receptor antagonists containing such refers to glucocorticoid receptor antagonists that do not share structural homology to, or are not modifications of, cortisol. Such compounds include synthetic mimetics and analogs of proteins, including partially peptidic, pseudopeptidic, and non-peptidic molecular entities.

Non-steroidal GRA compounds also include glucocorticoid receptor antagonists having a cyclohexyl-pyrimidine backbone, a fused azadecalin backbone, a heteroaryl ketone fused azadecalin backbone, or an octahydro fused azadecalin backbone. Exemplary glucocorticoid receptor antagonists having a cyclohexyl-pyrimidine backbone include those described in U.S. Pat. No. 8,685,973. Exemplary GRAs having a fused azadecalin backbone include those described in U.S. Pat. Nos. 7,928,237 and 8,461,172. Exemplary GRAs having a heteroaryl ketone fused azadecalin backbone include those described in U.S. Pat. Pub. 2014/0038926. Exemplary GRAs having an octohydro fused azadecalin backbone include those described in U.S. Provisional Patent Application No. 61/908,333, entitled Octahydro Fused Azadecalin Glucocorticoid Receptor Modulators, filed on Nov. 25, 2013.

Where substituent groups are specified by their conventional chemical formulae, written from left to right, they equally encompass the chemically identical substituents that would result from writing the structure from right to left, e.g., —CH2O— is equivalent to —OCH$_2$—.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, and hexyl.

"Alkoxy" refers to an alkyl group having an oxygen atom that connects the alkyl group to the point of attachment: alkyl-O—. As for the alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Halogen" refers to fluorine, chlorine, bromine, and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$, and include trifluoromethyl, fluoromethyl, etc.

The term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, and perfluoroethoxy.

"Cycloalkyl" refers to a saturated or partially unsaturated, monocyclic, fused bicyclic, or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene, and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic C3-8 cycloalkyl, exemplary groups include, but are not limited to, cyclopropyl, cyclobutyl, cyclopentyl, cyclohexyl, cycloheptyl, and cyclooctyl. When cycloalkyl is a saturated monocyclic $C_{3-6}$ cycloalkyl, exemplary groups include, but are not limited to, cyclopropyl, cyclobutyl, cyclopentyl, and cyclohexyl.

"Heterocycloalkyl" refers to a saturated ring system having from 3 to 12 ring members and from 1 to 4 heteroatoms of N, O, and S. Additional heteroatoms can also be useful, including but not limited to, B, Al, Si, and P. The heteroatoms can also be oxidized, such as, but not limited to, —S(O)— and —S(O)$_2$—. Heterocycloalkyl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as 6, 7, 8, 9, 10, 11, 12, 13, 14, 15, or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, that has a methylene linking group. Some aryl groups have from 6 to 12 ring members, such as phenyl, naphthyl, or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic, fused bicyclic, or tricyclic aromatic ring assembly containing 5 to 16 ring atoms, where from 1 to 5 of the ring atoms are a heteroatom such as N, O, or S. Additional heteroatoms can also be useful, including but not limited to, B, Al, Si, and P. The heteroatoms can also be oxidized, such as, but not limited to, N-oxide, —S(O)—, and —S(O)$_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5; or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4-, and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2-, and 3-pyrrole; pyridine includes 2-, 3- and 4-pyridine; imidazole includes 1-, 2-, 4- and 5-imidazole; pyrazole includes 1-, 3-, 4- and 5-pyrazole; triazole includes 1-, 4- and 5-triazole; tetrazole includes 1- and 5-tetrazole; pyrimidine includes 2-, 4-, 5- and 6- pyrimidine; pyridazine includes 3- and 4-pyridazine; 1,2,3-triazine includes 4- and 5-triazine; 1,2,4-triazine includes 3-, 5- and 6-triazine; 1,3,5-triazine includes 2-triazine; thiophene includes 2- and 3-thiophene; furan includes 2- and 3-furan; thiazole includes 2-, 4- and 5-thiazole; isothiazole includes 3-, 4- and 5-isothiazole; oxazole includes 2-, 4- and 5-oxazole; isoxazole includes 3-, 4- and 5-isoxazole; indole includes 1-, 2- and 3-indole; isoindole includes 1- and 2-isoindole; quinoline includes 2-, 3- and 4-quinoline; isoquinoline includes 1-, 3- and 4-isoquinoline; quinazoline includes 2- and 4-quinoazoline; cinnoline includes 3- and 4-cinnoline; benzothiophene includes 2- and 3-benzothiophene; and benzofuran includes 2- and 3-benzofuran.

Some heteroaryl groups include those having from 5 to 10 ring members and from 1 to 3 ring atoms including N, O, or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroatoms" refers to O, S, or N.

"Salt" refers to acid or base salts of the compounds used in the methods of the present invention. Illustrative examples of pharmaceutically-acceptable salts are mineral acid (hydrochloric acid, hydrobromic acid, phosphoric acid, and the like) salts, organic acid (acetic acid, propionic acid, glutamic acid, citric acid, and the like) salts, and quaternary ammonium (methyl iodide, ethyl iodide, and the like) salts. It is understood that the pharmaceutically-acceptable salts are non-toxic. Additional information on suitable pharmaceutically-acceptable salts can be found in Remington's Pharmaceutical Sciences, 17th ed., Mack Publishing Company, Easton, Pa., 1985, which is incorporated herein by reference.

"Isomers" refers to compounds with the same chemical formula but which are structurally distinguishable.

"Tautomer" refers to one of two or more structural isomers which exist in equilibrium and which are readily converted from one form to another.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to produce compounds which are not inherently unstable—and/or would be known to one of ordinary skill in the art as likely to be unstable under ambient conditions—such as aqueous, neutral, or physiological conditions.

"Pharmaceutically-acceptable excipient" and "pharmaceutically-acceptable carrier" refer to a substance that aids the administration of an active agent to—and absorption by—a subject and can be included in the compositions of the present invention without causing a significant adverse toxicological effect on the patient. Non-limiting examples of pharmaceutically-acceptable excipients include water, NaCl, normal saline solutions, lactated Ringer's, normal sucrose, normal glucose, binders, fillers, disintegrants, lubricants, coatings, sweeteners, flavors and colors, and the like. One of ordinary skill in the art will recognize that other pharmaceutical excipients are useful in the present invention.

III. Detailed Descriptions of Embodiments

A. Method For Differential Diagnosis of ACTH-Dependent Cushing's Syndrome

1. Selecting Patients Having ACTH-Dependent Cushing's Syndrome

The methods disclosed herein is used to provide differential diagnosis between Cushing Disease and Ectopic Cushing's Syndrome to patients who have already been diagnosed as having ACTH-dependent Cushing's Syndrome. A diagnosis of ACTH-dependent Cushing's Syndrome can be made based on observation of certain clinical symptoms, the detection of hypercortisolemia and elevated blood ACTH levels.

a. Clinical Symptoms

Eligible patients may exhibit one or more of the following symptoms: easy bruising; abdominal obesity and thin arms and legs; facial plethora; acne; proximal myopathy (or proximal muscle weakness); striae (especially if reddish purple and 1 cm wide); and thin skin. Patients may also frequently feel changes in mood; change in appetite, headaches; a chronic feeling of tiredness; osteoporosis; low potassium; hyperglycemia; diabetes, and high blood pressure; decreased concentration peripheral edema hypokalemia; decreased libido acne kidney stones; impaired memory (especially short term); and unusual infections. Females patients may have irregular menstruation, hirsutism, or female balding. Pediatric patients may have weight gain with decreasing growth velocity; abnormal genital virilization; short stature; and pseudoprecocious puberty or delayed puberty. The next step is to confirm these patients have hypercortisolemia.

b Hypercortisolemia

A diagnosis of hypercortisolemia requires the determination of the patient's circulating cortisol level. Various types of samples that can be used for this purpose, such as saliva, urine, whole blood, serum, and plasma. Samples may also be collected at different time during the day. In one approach, the patient's whole blood sample is collected and processed to collect serum or plasma, i.e., in the morning, e.g., between 8 am and 10 am. or in the afternoon, e.g., at 4 pm. The collected serum or plasma sample is refrigerated or frozen within, e.g., 2 hours of collection. Analysis of the serum or plasma sample is performed in a timely fashion, e.g. within 7 days from sample collection. In another approach, the patient's cortisol levels are measured from his or her saliva samples. Salivary cortisol is in equilibrium with the free cortisol in blood circulation. Changes of cortisol levels in the bloodstream are paralleled, within minutes, by similar alterations in salivary cortisol concentrations, such that one can use the latter as a surrogate of the former. The commonly used saliva-based cortisol test is the midnight saliva test, which measures cortisol levels from saliva samples collected at between 11 pm and midnight. Intake of food or drink is prohibited at least 15 minutes prior to sample collection. Saliva samples are collected by keeping and rolling a swab in mouth for approximately 2 minutes. The saliva samples, ambient or refrigerated, are then sent to a laboratory for cortisol level determination in a timely fashion, e.g., within 7 days from sample collection.

Methods for measuring cortisol levels are known to those in the art. Useful assays include immunoassays, e.g., competitive immunoassay, radioimmunoassay, immunofluorometric enzyme assay, and ELISA, competitive protein-binding assay and mass spectrometry, e.g., high-performance liquid chromatography/triple quadrupole-mass spectrometry (LC-MS/MS). Commercial kits for measuring cortisol in samples are available from Beckman-Coulter, Siemens, Roche Diagnostics, and the like. Non-limiting examples of cortisol tests are Mayo Clinic's SALCT, CORT, CORTU, and CINP tests; an ADVIA Centaur® Cortisol assay (Siemens Healthcare Global); ARCHITECT i2000SR cortisol (Abbott); Immulite® 2000 Cortisol assay (Siemens Healthcare Global; # L2KCO2), Vitros® ECi Cortisol assay (Ortho Clinical Diagnostics; #107 4053), and Elecsys® Cortisol Immunoassay (Roche Molecular Diagnostics; #11875116160).

The patient's cortisol measurement is then compared with the normal reference value and a level higher than the normal reference value indicates the patient has hypercortisolemia. The normal reference values for cortisol levels vary depending on the nature of the samples, the manner and timing of sample collection (higher for samples collected in the morning and lower for samples collected at night), and the detection method. Thus, it is essential to interpret test results in the context of the appropriate normal reference values. Various commercial kits provide the normal reference values in testing protocols. For example, normal reference values for the Mayo Clinic's SALCT test that determines cortisol level in saliva is <100 ng/dL; a saliva cortisol level higher than 100 ng/dL is thus an indication of hypercortisolemia. After being diagnosed with hypercortisolemia, the patient is subject to additional tests to confirm the presence of Cushing's Syndrome.

c Cushing's Syndrome

At least one, preferably two or more, of the following tests are performed to diagnose Cushing's Syndrome: 1) dexamethasone suppression test, which documents a loss of feedback inhibition of cortisol on the hypothalamic-pituitary-adrenal (HPA) axis; 2) 24-hour Urine Free Cortisol test, which assesses cortisol secretion in a 24-hour period; and 3) midnight salivary cortisol, which evaluates the loss of normal diurnal variation in cortisol secretion. If two of the three tests show abnormal cortisol levels, the Cushing's Syndrome is confirmed.

The dexamethasone suppression test is typically used as a screen test for Cushing's Syndrome. Dexamethasone is an exogenous steroid that binds glucocorticoid receptors in the anterior pituitary gland. When healthy individuals are treated with a low dose (1-2 mg) of dexamethasone, binding of dexamethasone to the glucocorticoid receptors provides negative feedback to the pituitary gland and results in suppression of ACTH secretion. The suppression of ACTH secretion, in turn, results in suppression of cortisol release and therefore a detectable decrease in cortisol level in circulation. In contrast, when patients having Cushing's Syndrome are treated with a low dose of dexamethasone, no or little decrease in cortisol levels can be detected because of the excessive cortisol production associated with the disease. In one approach, the dexamethasone suppression test is performed by administering a low dose of dexamethasone, e.g., 1 mg, the night before at, e.g., 11 pm. The next morning, e.g., between 8-9 am; the patient's blood is then sampled and serum cortisol levels measured. Since normal subjects typically have serum cortisol levels reduced to less than 1.8 mg/dl, a serum cortisol level of more than 1.8 mg/dL is indicative of the presence of Cushing's Syndrome, The 24-hour Urine Free Cortisol test is the gold standard for diagnosing Cushing's Syndrome. This test uses the principle that cortisol production is increased in patients having Cushing's Syndrome, and measurements of urinary excretion provide an integral estimate of that increase. A result more than the normal reference values is indicative of the presence of Cushing's Syndrome. A 3 to 4-fold increase over normal reference values provides definite diagnosis of Cushing's Syndrome; if this increase is present, no additional testing is required to confirm the diagnosis. For less dramatic increases in the urinary free-cortisol (UFC) level, other tests, such as the overnight dexamethasone suppression test and the midnight salivary cortisol test, as described above, are required.

The midnight saliva test is another test commonly used to confirm Cushing's Syndrome. The test is described in the section titled "hypercortisolemia", supra.

If the patient is confirmed to have Cushing's Syndrome by two of the three tests, or by the detection of a 3 to 4-fold cortisol level increase in the 24-hour Urine Free Cortisol test, the next step is to measure ACTH to confirm he or she has ACTH-dependent Cushing's Syndrome.

d ACTH-Dependent Cushing's Syndrome

There are two kinds of endogenous Cushing's Syndrome: ACTH-dependent and ACTH-independent. The high cortisol level associated with ACTH-dependent Cushing's Syndrome is caused by the overproduction of ACTH from a tumor, e.g., a pituitary tumor or an extrapituitary tumor. The excess cortisol level associated with ACTH-independent Cushing's Syndrome, on the other hand, is caused by the overproduction of cortisol by a tumor in the adrenal gland or the overgrowth of the adrenal gland—either of which inhibits ACTH production and release. Thus, the ACTH levels are high in patients having ACTH-dependent Cushing's Syndrome but low or even undetectable in patients having ACTH-independent Cushing's Syndrome.

The types of samples that are suitable for ACTH determination can be serum, plasma, saliva, urine, or any other biological fluid taken from a subject. The sample can be the same or different from the sample used for cortisol level measurement. In some cases, the same sample that is used to measure cortisol level can be used to measure ACTH level. In other cases, different samples are used to measure cortisol and ACTH levels. For example, the cortisol levels can be measured in saliva and the ACTH levels can be measured in plasma. In yet other cases, different samples of the same type are used to measure the levels.

The level of ACTH can be measured using various methods, including but not limited to, immunoassays, e.g., competitive immunoassay, radioimmunoassay, immunofluorometric enzyme assay, and ELISA; competitive protein-binding assays; liquid chromatography (e.g., HPLC); and mass spectrometry, e.g., high-performance liquid chromatography/triple quadrupole-mass spectrometry (LC-MS/MS). Commercial kits for measuring ACTH are readily available, e.g., from Mayo clinic (Test ID: ACTH), Siemens Healthcare Global (Immulite® 2000 ACTH assay), and Roche Molecular Diagnostics (Catalog No. 03255751190).

A plasma ACTH concentration higher than the normal reference value indicates that the patient has ACTH-dependent Cushing's Syndrome. Normal reference values vary depending on the assay method, type of sample, as well as the timing of sample collection because, like cortisol, ACTH in healthy individuals varies during a 24-hour period, reaching its highest level in the morning around 6-8 am and lowest at night around 11 pm. Various commercial kits provide the normal reference values in their testing protocols. For example, the normal reference values for Mayo Clinic Test ID: ACTH are about 10-60 pg/mL.

Patients diagnosed with ACTH-dependent Cushing's Syndrome are selected for the differential diagnosis as described below.

2. Method of Differential Diagnosis of ACTH-Dependent Cushing's Syndrome

The differential diagnosis method uses GRAs to discriminate between Cushing Disease and Ectopic Cushing's Syndrome, the two major forms of ACTH-dependent Cushing's Syndrome. In patients having ACTH-dependent Cushing's Syndrome, the presence of excess cortisol inhibits normal pituitary tissue's role in promoting ACTH production and secretion. The effect of GRA treatment on these patients are two-fold: on one hand, GRA acts on the pituitary gland to increase the production of biologically active ACTH, i.e., ACTH that can stimulate cortisol production and/or secretion, which can increase cortisol levels. Fleseriu et al., *J. Clin. Endocrinol. Metab.* 2012 June 97 (6): 2039-49. On the other hand, GRA blocks the signaling of the autocrine cortisol receptors in adrenocortical cells—the cortisol-producing cells,—to lower cortisol levels. See, Asser et al., *Mol Cell Endocrinol*. 395 (2014) 1-9; Albertson et al., *Eur. J. of Endocrinol.*, 1994 (130): 195-200.

The diagnosis method is based on the surprising discovery that the effects of GRA treatment on cortisol and ACTH production and secretion in patients having Cushing' Disease are very different from those in patients having Ectopic Cushing's Syndrome. For patients having Cushing's Disease, the positive effect of GRA on cortisol level—through the stimulation of excess production of biologically active ACTH, which causing the increase in cortisol production and secretion—significantly outweighs the negative effect of the GRA on cortisol production—through the inhibition of cortisol production by the adrenocortical cells. This results in an increase of the ratio of cortisol to ACTH levels. In contrast, patients having ectopic ACTH secreting tumors produce excessive amounts of ACTH; but the majority of which is biologically inactive and the high levels of circulating cortisol also suppress the pituitary gland's natural ability to generate biologically active ACTH. As a result, active ACTH is relatively unchanged after treatment with GRAs in these patients and thus would not affect cortisol production and secretion. However, GRAs can still inhibit the cortisol production by the adrenocortical cells through inhibition of several steroidogenesis enzymes (Asser et al., Mol. Cell. Endocrino., 2014 September 395(1-2):1-9), which result in a decrease of cortisol level and a decrease of the ratio of cortisol to ACTH levels. Thus the change of the C:A ratio after the GRA treatment can serve as a basis for the differential diagnosis: an increase in the C:A ratio of greater than 50% after GRA treatment indicates Cushing's Disease and a decrease in the C:A ratio of greater than 50% after GRA treatment corresponds to Ectopic Cushing's Syndrome.

a. Sampling

Various types of samples that can be used for this purpose, such as saliva, urine, whole blood, serum, and plasma. Samples may also be collected at different time during the day. In one approach, the patient's whole blood sample is collected and processed to collect serum or plasma, i.e., in the morning, e.g., at 8 am or in the afternoon, e.g., at 4 pm. The collected serum sample is refrigerated or frozen within, e.g., 2 hours of collection. In one approach, saliva samples are collected by keeping and rolling a swab in mouth for approximately 2 minutes, at a time between 11 pm and midnight. Intake of food or drink is prohibited at least 15 minutes prior to sample collection. The samples, typically refrigerated or frozen, are then sent to a laboratory to assess the cortisol and ACTH levels in a timely fashion, e.g., within 7 days from sample collection.

The differential diagnosis method disclosed herein involves taking one or more pretreatment samples (before the GRA treatment) and one or more second samples (after the GRA treatment) from a patient. In some embodiments, the pretreatment sample(s) and the second sample(s) from the patient are of the same type, e.g., plasma, from which both the cortisol and ACTH levels are determined. In some embodiments, different types of samples are collected for measuring cortisol and ACTH levels. For example, 24-hour urine collections before and after the GRA treatment are used for measuring the cortisol levels and plasma samples before and after the GRA treatment are used for measuring the ACTH levels.

Pretreatment samples are taken from the patient before the start of the GRA treatment. In some embodiments, a pretreatment sample is taken within 1, 2, 3, 4, 5, or 6 weeks prior to the administration of GRA. In some embodiments, a pretreatment sample is taken on the same day, within a few hours before administration of GRA. In some embodiments, the pretreatment sample is taken less than 1 hour, or 30 min, or 10 min before the first dose of GRA is administered. Second samples are collected from the patient at the end of a period during which the patient has been treated with GRA. In some embodiments, the period after which the second samples are taken is 6 weeks or longer, e.g., 6-10 weeks. In some embodiments, the period is 2, 3, 4 or more months.

b Administration of GRA

The GRA compounds or compositions of the present invention can be delivered by any suitable means, including oral, parenteral (e.g., intravenous injection or intramuscular injection or infusion) and topical methods. Transdermal administration methods, by a topical route, can be formulated as applicator sticks, solutions, suspensions, emulsions, gels, creams, ointments, pastes, jellies, paints, powders, and aerosols. GRAs can be administered orally as a pill, a capsule, or liquid formulation as described herein.

In some embodiments, the GRA is administered in one dose. In other embodiments, the GRA is administered in more than one dose, e.g., 2 doses, 3 doses, 4 doses, 5 doses, 6 doses, 7 doses, or more. In some cases, the doses are of an equivalent amount. In other cases, the doses are of different amounts. The doses can increase or taper over the duration of administration. The amount will vary according to, for example, the GRA properties. To determine an effective dose, the GRA must elevate the level of ACTH by at least two fold in a healthy individual. In one embodiment, the GRA is mifepristone. In one embodiment, the mifepristone is administered at 300-1500 mg to the patient. In one embodiment, mifepristone is administered on a daily basis equal to 5-20 mg/kg of patient.

c. Diagnosis Based on the Comparison of the Baseline C:A Ratio and the GRA-Exposed C:A Ratio The ACTH levels and cortisol levels are determined using the methods as described in the above section titled "Selecting Patients Having ACTH-Dependent Cushing's Syndrome". Baseline cortisol/ACTH levels are determined from the pretreatment samples and second cortisol/ACTH levels are determined from second samples from each patient. The baseline C:A ratio is calculated from the baseline cortisol and the baseline ACTH levels, and the GRA-exposed C:A ratio is calculated from the second (GRA-exposed) cortisol and the second (GRA-exposed) ACTH levels. If the GRA-exposed C:A ratio has decreased by greater than 50% compared to the baseline C:A ratio, the patient is diagnosed as having Ectopic Cushing's Syndrome. If the GRA-exposed C:A ratio has increased by greater than 50% compared to the baseline C:A ratio, the patient is diagnosed as having Cushing's Disease.

B. Glucocorticoid Receptor Antagonists

The methods of the present invention generally provide administering a GRA. In some cases, the glucocorticoid receptor antagonist is a specific GRA. As used herein, a specific glucocorticoid receptor antagonist refers to a composition or compound which inhibits any biological response associated with the binding of a glucocorticoid receptor to an agonist by preferentially binding to the glucocorticoid receptor rather than to another nuclear receptor (NR). In some embodiments, the specific GRA binds preferentially to the glucocorticoid receptor rather than the mineralocorticoid receptor (MR), androgen receptor (AR), or progesterone receptor (PR). In an exemplary embodiment, the specific GRA binds preferentially to glucocorticoid receptor rather than the mineralocorticoid receptor (MR). In another exemplary embodiment, the specific GRA binds preferentially to the glucocorticoid receptor rather than the progesterone receptor (PR). In another exemplary embodiment, the specific GRA binds preferentially to the glucocorticoid receptor rather than the androgen receptor (AR). In yet another exemplary embodiment, the specific GRA binds preferentially to the glucocorticoid receptor in comparison to MR and PR, MR and AR, PR and AR, or MR, PR, and AR.

In a related embodiment, the specific GRA binds to the glucocorticoid receptor with an association constant ($K_d$) that is at least 10-fold less than the $K_d$ for other nuclear receptors. In another embodiment, the specific GRA binds to the glucocorticoid receptor with an association constant ($K_d$) that is at least 100-fold less than the $K_d$ for the other nuclear receptors. In another embodiment, the specific GRA binds to the glucocorticoid receptor with an association constant ($K_d$) that is at least 1000-fold less than the $K_d$ for the other nuclear receptors.

Generally, treatment can be provided by administering an effective amount of a GRA of any chemical structure or mechanism of action and a glucocorticosteroid of any chemical structure or mechanism of action. Provided herein, are classes of exemplary GRAs and specific members of such classes. However, one of skill in the art will readily recognize other related or unrelated GRAs that can be employed in the treatment methods described herein.

1. GRAs Having a Steroidal Backbone

In some embodiments, an effective amount of a GRA with a steroidal backbone is administered to a subject for treatment of an ACTH-secreting tumor. Steroidal GRAs can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create GRAs include modifications of the 11-β hydroxy group and modification of the 17-β side chain (See, e.g., Lefebvre, J. Steroid Biochem. 33:557-563, 1989).

Examples of steroidal GR antagonists include androgen-type steroidal compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, 5,696,127, and 6,303,591. Such steroidal GR antagonists include cortexolone, dexamethasone-oxetanone, 19-nordeoxycorticosterone, 19-norprogesterone, cortisol-21-mesylate; dexamethasone-21-mesylate, 11β-(4-dimethylaminoethoxyphenyl)-17α-propynyl-17β-hydroxy-4,9-estradien-3-one (RU009), and (17α)-17-hydroxy-19-(4-methylphenyl)androsta-4,9 (11)-dien-3-one (RU044).

Other examples of steroidal antiglucocorticoids are disclosed in Van Kampen et al. (2002) Eur. J. Pharmacol. 457(2-3):207, WO 03/043640, EP 0 683 172 B1, and EP 0 763 541 B1, each of which is incorporated herein by reference. EP 0 763 541 B1 and Hoyberg et al., Int'l J. of Neuro-psychopharmacology, 5:Supp. 1, 5148 (2002) disclose the compound (11β,17β-11-(1,3-benzodioxol-5-yl)-17-hydroxy-17-(1-propynyl)estra-4,9-dien-3-one (ORG 34517), which in one embodiment, is administered in an amount effective to treat an ACTH-secreting tumor in a subject.

2. Removal or Substitution of the 11-β Hydroxy Group

Glucocorticoid antagonists with modified steroidal backbones comprising removal or substitution of the 11-β hydroxy group are administered in one embodiment of the invention. This class includes natural GRAs, including cortexolone, progesterone and testosterone derivatives, and synthetic compositions, such as mifepristone (Lefebvre, et al. supra). Preferred embodiments of the invention include all 11-β aryl steroid backbone derivatives because, in some cases, these compounds can be devoid of progesterone receptor (PR) binding activity (Agarwal, FEBS 217:221-226, 1987). In another embodiment an 11-β phenyl-aminodimethyl steroid backbone derivative, which is both an effective anti-glucocorticoid and anti-progesterone agent, is administered. These compositions can act as reversibly-binding steroid receptor antagonists. For example, when bound to a 11-β phenyl-aminodimethyl steroid, the steroid receptor can be maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-β-hydrox-11-β-(4-dimethyl-aminophenyl)17-α-(1-propynyl)estra-4,9-dien-3-one). Mifepristone has been shown to be a powerful antagonist of both the progesterone and glucocorticoid (GR) receptors. Thus, in some embodiments, the GRA administered to treat an ACTH-secreting tumor is mifepristone, or a salt, tautomer, or derivative thereof. In other embodiments, however, administration of mifepristone is specifically excluded as a GRA for treatment of an ACTH-secreting tumor.

Another 11-β phenyl-aminodimethyl steroid shown to have GR antagonist effects includes the dimethyl aminoethoxyphenyl derivative RU009 (RU39.009), 11-β-(4-dimethyl-aminoethoxyphenyl)-17-α-(propynyl-17-β-hydroxy-4,9-estradien-3-one) (see Bocquel, J. Steroid Biochem. Molec. Biol. 45:205-215, 1993). Another GR antagonist related to RU486 is RU044 (RU43.044) 17-β-hydrox-17-α-19-(4-methyl-phenyl)-androsta-4,9(11)-dien-3-one) (Bocquel, 1993, supra). See also Teutsch, Steroids 38:651-665, 1981; U.S. Pat. Nos. 4,386,085 and 4,912,097.

One embodiment includes compositions that are irreversible anti-glucocorticoids. Such compounds include α-ketomethanesulfonate derivatives of cortisol, including cortisol-21-mesylate (4-pregnene-11-β, 17-α, 21-triol-3, 20-dione-21-methane-sulfonate and dexamethasone-21-mesylate (16-methyl-9-α-fluoro-1,4-pregnadiene-11 β, 17αa, 21-triol-3, 20-dione-21-methane-sulfonte). See Simons, J. Steroid Biochem. 24:25-32, 1986; Mercier, J. Steroid Biochem. 25:11-20, 1986; U.S. Pat. No. 4,296,206.

3. Modification of the 17-Beta Side Chain Group

Steroidal anti-glucocorticoids which can be obtained by various structural modifications of the 17-β side chain are also used in the methods of the invention. This class includes synthetic antiglucocorticoids, such as dexamethasone-oxetanone, various 17, 21-acetonide derivatives and 17-beta-carboxamide derivatives of dexamethasone (Lefebvre, 1989, supra; Rousseau, Nature 279:158-160, 1979).

4. Other Steroid Backbone Modifications

GRAs used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, Endocrinology 107:1278-1280, 1980).

In general, the 11-βside chain substituent, and particularly the size of that substituent, can play a key role in determining the extent of a steroid's anti-glucocorticoid activity. Substitutions in the A ring of the steroid backbone can also be important. For example, 17-hydroxypropenyl side chains can, in some cases, decrease anti-glucocorticoid activity in comparison to 17-propynyl side chain containing compounds.

Additional glucocorticoid receptor antagonists known in the art and suitable for practice of the invention include 21-hydroxy-6,19-oxidoprogesterone (See Vicent, Mol. Pharm. 52:749-753, 1997), Org31710 (See Mizutani, J Steroid Biochem Mol. Biol. 42(7):695-704, 1992), RU43044, RU40555 (See Kim, J Steroid Biochem Mol. Biol. 67(3):213-22, 1998), and RU28362.

5. Non-Steroidal Anti-Glucocorticoids as Antagonists

Non-steroidal glucocorticoid receptor antagonists (GRAs) are also used in the methods of the invention for the differential diagnosis of patients with ACTH dependent Cushing's Syndrome in a subject, where the differential diagnosis is between Ectopic Cushing's Syndrome and Cushing's Disease. These include synthetic mimetics and analogs of proteins, including partially peptidic, pseudopeptidic and non-peptidic molecular entities. For example, oligomeric peptidomimetics useful in the invention include (α-β-unsaturated) peptidosulfonamides, N-substituted glycine derivatives, oligo carbamates, oligo urea peptidomimetics, hydrazinopeptides, oligosulfones and the like (See, e.g., Amour, Int. J. Pept. Protein Res. 43:297-304, 1994; de Bont, Bioorganic & Medicinal Chem. 4:667-672, 1996).

Examples of non-steroidal GR antagonists include the GR antagonist compounds disclosed in U.S. Pat. Nos. 5,696, 127; 6,570,020; and 6,051,573; the GR antagonist compounds disclosed in US Patent Application 20020077356, the glucocorticoid receptor antagonists disclosed in Bradley et al., J. Med. Chem. 45, 2417-2424 (2002), e.g., 4α(S)-benzyl-2(R)-chloroethynyl-1,2,3,4,4α,9,10,10α(R)-octahydro-phenanthrene-2,7-diol ("CP 394531") and 4α(S)-benzyl-2(R)-prop-1-ynyl-1,2,3,4,4α,9,10,10α(R)-octahydro-phenanthrene-2,7-diol ("CP 409069"); and the compounds disclosed in PCT International Application No. WO 96/19458, which describes non-steroidal compounds that are high-affinity, highly selective antagonists for steroid receptors, such as 6-substituted-1,2-dihydro-N-protected-quinolines.

In some embodiments, the subject is treated with an effective amount of a non-steroidal GRA having a cyclohexyl-pyrimidine backbone, a fused azadecalin backbone, a heteroaryl ketone fused azadecalin backbone, or an octahydro fused azadecalin backbone. For example, the patient can be treated with effective amounts of one of the foregoing GRAs and a GC or a GC analog. Exemplary GRAs having a cyclohexyl-pyrimidine backbone include those described in U.S. Pat. No. 8,685,973. In some cases, the GRA having a cyclohexyl-pyrimidine backbone has the following structure:

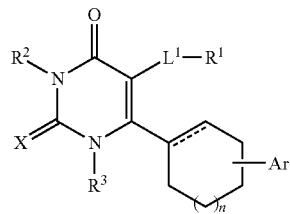

wherein
the dashed line is absent or a bond;
X is selected from the group consisting of O and S;
$R^1$ is selected from the group consisting of cycloalkyl, heterocycloalkyl, aryl and heteroaryl, optionally substituted with from 1 to 3 $R^{1a}$ groups;
each $R^{1a}$ is independently selected from the group consisting of H, $C_{1-6}$ alkyl, $C_{2-6}$ alkenyl, $C_{2-6}$ alkynyl, $C_{1-6}$ alkoxy, $C_{1-6}$ alkyl-$OR^{1b}$, halogen, $C_{1-6}$ haloalkyl, $C_{1-6}$ haloaloxy, $-OR^{1b}$, $-NR^{1b}R^{1c}$, $-C(O)R^{1b}$, $-C(O)OR^{1b}$, $-OC(O)R^{1b}$, $-C(O)NR^{1b}R^{1c}$, $-NR^{1b}C(O)R^{1c}$, $-SO_2R^{1b}$, $-SO_2NR^{1b}R^{1c}$, cycloalkyl, heterocycloalkyl, aryl and heteroaryl;
$R^{1b}$ and $R^{1c}$ are each independently selected from the group consisting of H and $C_{1-6}$ alkyl;
$R^2$ is selected from the group consisting of H, $C_{1-6}$ alkyl, $C_{1-6}$ alkyl-$OR^{1b}$, $C_{1-6}$ alkyl-$NR^{1b}R^{1c}$ and $C_{1-6}$ alkylene-heterocycloalkyl;
$R^3$ is selected from the group consisting of H and $C_{1-6}$ alkyl;
Ar is aryl, optionally substituted with 1-4 $R^4$ groups;
each $R^4$ is independently selected from the group consisting of H, $C_{1-6}$ alkyl, $C_{1-6}$ alkoxy, halogen, $C_{1-6}$ haloalkyl and $C_{1-6}$ haloalkoxy;
$L^1$ is a bond or $C_{1-6}$ alkylene; and subscript n is an integer from 0 to 3,
or a salts and isomers thereof.

Exemplary GRAs having a fused azadecalin backbone include those described in U.S. Pat. Nos. 7,928,237; and 8,461,172. In some cases, the GRA having a fused azadecalin backbone has the following structure:

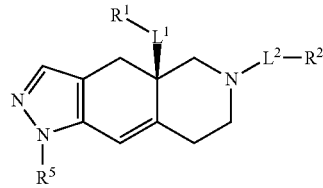

wherein
$L^1$ and $L^2$ are members independently selected from a bond and unsubstituted alkylene;
$R^1$ is a member selected from unsubstituted alkyl, unsubstituted heteroalkyl, unsubstituted heterocycloalkyl, $-OR^{1A}$, $-NR^{1C}R^{1D}$, $-C(O)NR^{1C}R^{1D}$, and $-C(O)OR^{1A}$, wherein
$R^{1A}$ is a member selected from hydrogen, unsubstituted alkyl and unsubstituted heteroalkyl,
$R^{1C}$ and $R^{1D}$ are members independently selected from unsubstituted alkyl and unsubstituted heteroalkyl,
wherein $R^{1C}$ and $R^{1D}$ are optionally joined to form an unsubstituted ring with the nitrogen to which they are attached, wherein said ring optionally comprises an additional ring nitrogen;

$R^2$ has the formula:

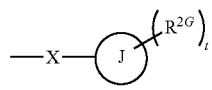

wherein $R^{2G}$ is a member selected from hydrogen, halogen, unsubstituted alkyl, unsubstituted heteroalkyl, unsubstituted cycloalkyl, unsubstituted heterocycloalkyl, —CN, and —CF$_3$;

J is phenyl;

t is an integer from 0 to 5;

X is —S(O$_2$)—; and $R^5$ is phenyl optionally substituted with 1-5 $R^{5A}$ groups, wherein $R^{5A}$ is a member selected from hydrogen, halogen, —OR$^{5A1}$, —S(O$_2$)NR$^{5A2}$R$^{5A3}$, —CN, and unsubstituted alkyl, wherein $R^{5A1}$ is a member selected from hydrogen and unsubstituted alkyl, and $R^{5A2}$ and $R^{5A3}$ are members independently selected from hydrogen and unsubstituted alkyl, or salts and isomers thereof.

Exemplary GRAs having a heteroaryl ketone fused azadecalin backbone include those described in U.S. 2014/0038926. In some cases, the GRA having a heteroaryl ketone fused azadecalin backbone has the following structure:

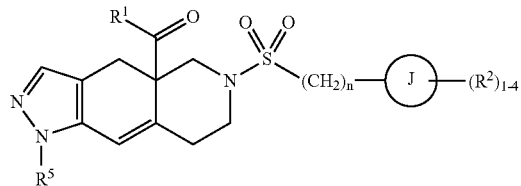

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;

each $R^{1a}$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, —CN, N-oxide, C$_{3-8}$ cycloalkyl, and C$_{3-8}$ heterocycloalkyl;

ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;

each $R^2$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, C$_{1-6}$ alkyl-C$_{1-6}$ alkoxy, —CN, —OH, —NR$^{2a}$R$^{2b}$, —C(O)R$^{2a}$, —C(O)OR$^{2a}$, —C(O)NR$^{2a}$R$^{2b}$, —SR$^{2a}$, —S(O)R$^{2a}$, —S(O)$_2$R$^{2a}$, C$_{3-8}$ cycloalkyl, and C$_{3-8}$ heterocycloalkyl, wherein the heterocycloalkyl groups are optionally substituted with 1-4 $R^{2c}$ groups;

alternatively, two $R^2$ groups linked to the same carbon are combined to form an oxo group (=O);

alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;

$R^{2a}$ and $R^{2b}$ are each independently selected from the group consisting of hydrogen and C$_{1-6}$ alkyl;

each $R^{2c}$ is independently selected from the group consisting of hydrogen, halogen, hydroxy, C$_{1-6}$ alkoxy, C$_{1-6}$ haloalkoxy, —CN, and —NR$^{2a}$R$^{2b}$;

each $R^{2d}$ is independently selected from the group consisting of hydrogen and C$_{1-6}$ alkyl, or two $R^{2d}$ groups attached to the same ring atom are combined to form (=O);

$R^3$ is selected from the group consisting of phenyl and pyridyl, each optionally substituted with 1-4 $R^{3a}$ groups;

each $R^{3a}$ is independently selected from the group consisting of hydrogen, halogen, and C$_{1-6}$ haloalkyl; and subscript n is an integer from 0 to 3;

or salts and isomers thereof.

Exemplary GRAs having an octohydro fused azadecalin backbone include those described in U.S. Provisional Patent Application No. 61/908,333, entitled Octahydro Fused Azadecalin Glucocorticoid Receptor Modulators, filed on Nov. 25, 2013. In some cases, the GRA having an octohydro fused azadecalin backbone has the following structure:

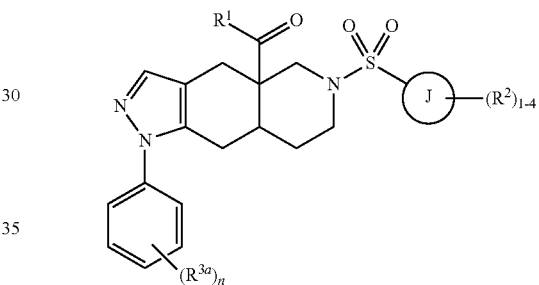

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;

each $R^{1a}$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, N-oxide, and C$_{3-8}$ cycloalkyl;

ring J is selected from the group consisting of an aryl ring and a heteroaryl ring having from 5 to 6 ring members and from 1 to 4 heteroatoms each independently selected from the group consisting of N, O and S;

each $R^2$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, C$_{1-6}$ alkyl-C$_{1-6}$ alkoxy, —CN, —OH, —NR$^{2a}$R$^{2b}$, —C(O)R$^{2a}$, —C(O)OR$^{2a}$, —C(O)NR$^{2a}$R$^{2b}$, —SR$^{2a}$, S(O)R$^{2a}$, —S(O)$_2$R$^{2a}$, C$_{3-8}$ cycloalkyl, and C$_{3-8}$ heterocycloalkyl having from 1 to 3 heteroatoms each independently selected from the group consisting of N, O and S;

alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups;

$R^{2a}$, $R^{2b}$ and $R^{2c}$ are each independently selected from the group consisting of hydrogen and C$_{1-6}$ alkyl;

each $R^{3a}$ is independently halogen; and subscript n is an integer from 0 to 3;

or salts and isomers thereof.

D. Pharmaceutical Compositions of Glucocorticoid Receptor Antagonists

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The GRA compositions of the present disclosure can be prepared in a wide variety of oral, parenteral and topical dosage forms. Oral preparations of either include tablets, pills, powder, dragées, capsules, liquids, lozenges, cachets, gels, syrups, slurries, suspensions, etc., suitable for ingestion by the patient. The GRA compositions of the present invention can also be administered by injection, that is, intravenously, intramuscularly, intracutaneously, subcutaneously, intraduodenally, or intraperitoneally. Also, the GRA compositions described herein can be administered by inhalation, for example, intranasally. Additionally, the GRA compositions of the present invention can be administered transdermally. The GRA compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention provides pharmaceutical compositions of a GRA including a pharmaceutically-acceptable carrier or excipient and a GRA compound of the present invention.

For preparing pharmaceutical compositions from the GRA compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragée cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving one or more compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The GRA compositions provided herein can also be delivered as microspheres for slow release in the body. For example, microspheres can be formulated for administration via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao, *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In another embodiment, the GRA compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These GRA formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the GRA formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

The GRA composition can also contain other compatible therapeutic agents. The compounds described herein can be used in combination with one another, with other active agents known to be useful in antagonizing a glucocorticoid receptor, or with adjunctive agents that may not be effective alone, but may contribute to the efficacy of the active agent.

IV. Systems

In one aspect, systems are provided for facilitating differential diagnosis between Ectopic Cushing's Syndrome and Cushing's Disease. Such systems can include one or more computing devices and can be communicatively coupled to a network. Such computing device can include a discrete computing device, a computing device tied into a main-frame system of a medical facility or can include one or more portable devices that are communicatively coupled to a network or server associated with a treating physician or medical facility. In some embodiments, one or more of the computing devices can include a portable computing device of a treating physician, such as a tablet or handheld device. Such systems are configured, typically with programmed instructions recorded on a memory thereof, to determine a relationship between a first set of values corresponding to and a second set of values and output a positive diagnosis as to Ectopic Cushing's Syndrome or Cushing's Disease based on the differential relationship. In some embodiments, the system includes a comparison engine that determines the differential relationship between the first and second set of values. The comparison engine can be defined by programmable instructions recorded on a memory of the system, which can include a memory accessed through a server or a memory coupled with one or more processors of one or more computing devices of the system.

Provided below are descriptions of some devices (and components of those devices) that may be used in the systems and methods described above. These devices may be used, for instance, to communicate, process, and/or store data related to any of the functionality described above. As will be appreciated by one of ordinary skill in the art, the devices described below may have only some of the components described below, or may have additional components.

FIG. 1 depicts an example block diagram of a system configured to determine a differential diagnosis between Ectopic Cushing's Syndrome and Cushing's Disease. In the illustrated embodiment, differential diagnostic system 100 includes a computer system 115 coupled to a network or server 110 that includes medical data associated with the patient from one or more data sources 105 (e.g. laboratory output of sample results). Data sources 105 can include the first and second set of values corresponding to analytical results of samples obtained from the patient. The techniques described herein are not limited to any particular type of computer system or computer network and could include one or more computing devices, including portable computing devices. For example, network 110 can be a local area network (LAN), a wide-area network (WAN), a wireless network, a bus connection, an interconnect, or any other means of communicating data or control information across one or more transmission lines or traces in an electronic system. While in this embodiment, data sources 105 are accessed through a network or server 110, it is appreciated that data sources 105 can communicate data directly to the computing system 115 or data can be manually input into computer system 115 through a user input.

Computer system 115 includes a processor 101 and a system memory 104 coupled together via an interconnect bus 108. In some embodiments, processor 101 and system memory 104 can be directly interconnected, or can be connected indirectly through one or more intermediary components or units. Processor 101 and system memory 104 can be any general-purpose or special-purpose components as is known in the art and is not limited to any particular type of processor or memory system. System memory 104 can be configured to store system and control data for automatically performing the diagnostic methods described herein. In some embodiments, computing system 115 is coupled with a database 135 (internal or external) to receive data. The data stored on database 135 can include data values corresponding to the first and second set of samples of the patient or data pertaining to the determination of a differential relationship between the first and second set of values. For example, the processor can perform a differential diagnosis based on whether the ratio of cortisol to ACTH has increased or decreased by a pre-determined or set percentage as compared to the baseline ratio of cortisol to ACTH. This percentage can be stored on system memory 104, or can be automatically obtained from database 135 as needed or obtained from another data source 105 accessed through communication with network 110. One advantage to including programmable instructions that queries an external data source for the set or pre-determined percentage is that the set percentage can be changed or updated periodically, as needed, without altering the configuration of computing system 115.

Computing system 115 receives input data 103 from the various data sources through communications interface 120. Computer system 115 processes the received data according to programmed instructions recorded on memory 104 and provides resulting data pertaining to the differential diagnosis to a user via output module 125. Output module 125 can be communicatively coupled to a user interface display or printer for presenting the processed data pertaining to the differential diagnosis. Typically, the output module 125 outputs an indication representing the differential diagnosis to the user (e.g. "positive diagnosis for Ectopic Cushing's Syndrome," "positive diagnosis for Cushing's Disease," "inconclusive") based on the received data pertaining to the differential diagnosis. Output module can further output data pertaining to the differential relationship between first and second values (e.g. "ratio increase exceeds 50% of baseline," "ratio increase exceeds 60% of baseline"). In another aspect, the output module 125 can output the processed data directly to the network 110 or to a health information database 135 so that the differential diagnosis or associated data can be accessed by various other computing devices communicatively coupled with the network or database.

In some embodiments, the computing system 115 receives a first set of data values from data sources 105 that represent baseline levels of cortisol and ACTH of a patient, via network 110, and provides those values to comparison engine 130. Computing system 115 then receives a second set of data values representing levels of cortisol and ACTH in the patient post-treatment with GRA and provides those values to the comparison engine 130. Comparison engine 130 then causes the processor 101 to determine a differential relationship between the first and second set of values and to determine if there has been a change in cortisol and ACTH levels due to treatment with GRA. The processor is then configured to determines a differential diagnosis of Cushing's Ectopic Syndrome or Cushing's Disease based on the determined differential relationship.

Specifically, comparison engine 130 can include a processor coupled with a memory having recorded thereon executable programmable instructions that cause processor 101 to determine a differential relationship between received first and second sets of values. In one aspect, the differential relationship is a change in a ratio of cortisol to ACTH between the baseline and post-treatment relative the baseline ratio of cortisol to ACTH. In some embodiments, the first and second sets of values are designated in the memory of the comparison engine as corresponding to baseline and post-treatment values, respectively. If the change in the ratio is an increase by a pre-determined threshold, the output module 125 outputs an indication representing a positive diagnosis for Ectopic Cushing's Syndrome. If the change in ratio is a decrease by a pre-determined threshold, then the output module 125 outputs an indication representing a positive diagnosis for Cushing's Disease. In some embodiments, the pre-determined threshold is a percentage of the baseline ratio. In some embodiments, the pre-determined threshold is a percentage greater than 20%, such as greater than 30%, greater than 40%, greater than 50% or greater than 60% or more. In some embodiments, the pre-determined threshold is the same for both a determined increase and decrease of the ratio, while in others the pre-determined threshold can be different for increase and decreases of the ratio.

In some embodiments, comparison engine 130 compares each value of the baseline cortisol and ACTH levels received in the first set of data values with a corresponding value of the post-treatment cortisol and ACTH levels to determine whether they are equal or different. In one embodiment, if a difference is determined between the two values by the comparison engine 130, an output signal indicating as such may be effected by the comparison engine. Similarly, in an alternate embodiment, if the two values are determined to be equal or if a change in ratio is less than a pre-determine threshold, a signal indicating as such can be output by the output module indicating that the differential diagnosis is indeterminate. In another aspect, comparison engine can determine a baseline ratio of cortisol to ACTH and a post-treatment ratio of cortisol to ACTH and compare the two ratios relative a reference, such as the baseline ratio.

Comparison engine 130 may be implemented using specially configured computer hardware or circuitry or general-purpose computing hardware programmed by specially designed software modules or components; or any combination of hardware and software. The techniques described herein are not limited to any specific combination of hardware circuitry or software. For example, comparison engine 130 may include off-the-shelf comparator circuitry components or custom-designed comparator circuitry. The comparator circuitry is configured to compare two or more values (e.g. ratios) and to output a result as to a difference between the values relative to the first value. Alternatively, the comparison functionality may be performed in software stored in memory 104 and executed by the processor 101.

Figure 2:
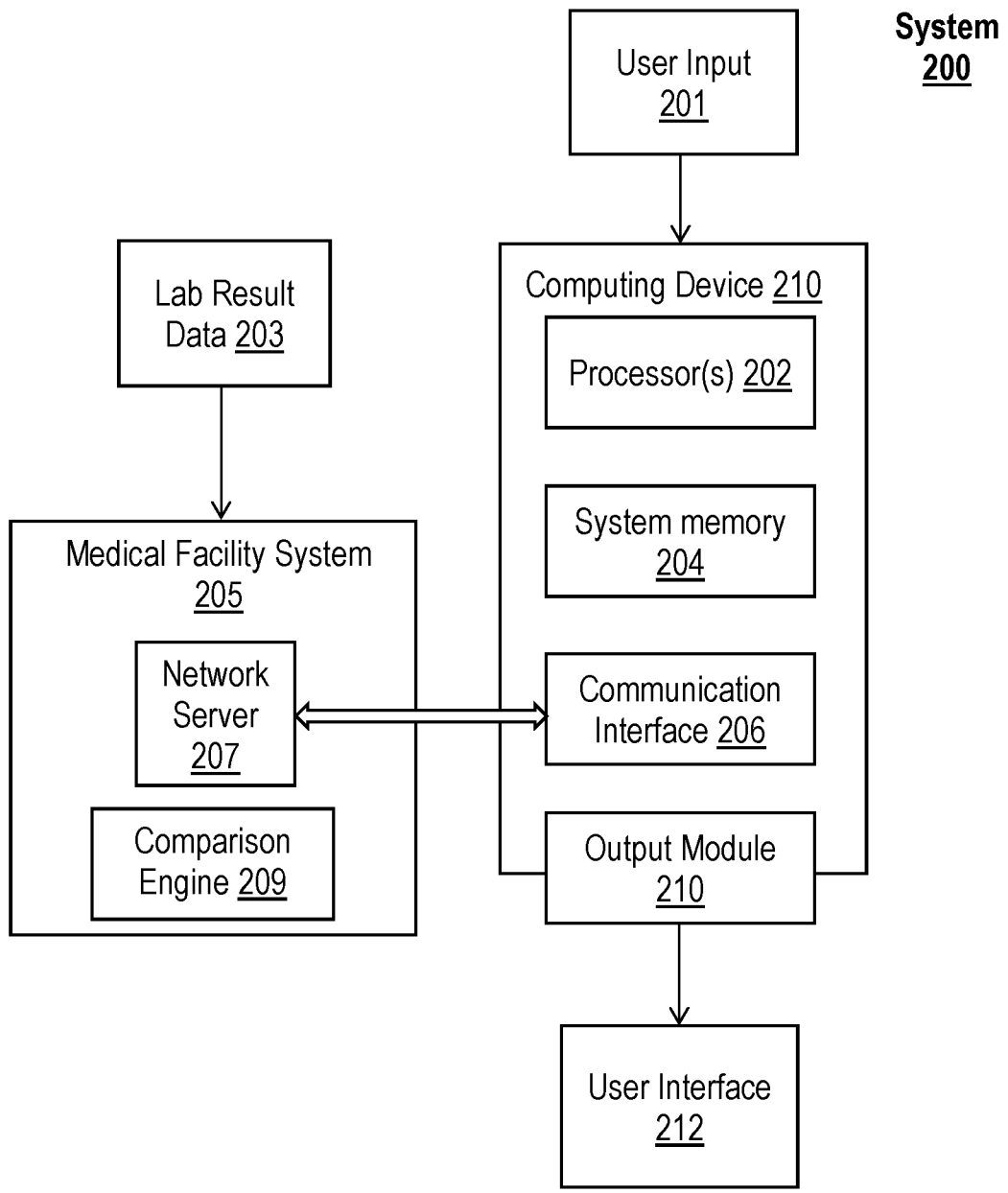
FIG. 2 shows an alternative system adapted for differentially diagnosing Cushing's Disease from Ectopic Cushing's Syndrome in accordance with various embodiments.

FIG. 2 depicts an example block diagram of an alternative System 200 configured for differential diagnosis between Ectopic Cushing's Syndrome and Cushing's Disease. In this embodiment, the Comparison Engine 209 is located on a computing system of a Medical Facility System 205 and is accessed through Network Server 207, which is advantageous as it allows the Medical Facility to control and update determinations affecting differential diagnosis from a central location. It is further appreciated that the Comparison Engine 209 could be located on yet another computing system accessed through another server, for example that of a developer of GRA that may have access to updated data regarding clinical data and diagnostics sooner than would the medical facility.

In the illustrated embodiment, System 200 includes a Computing Device 210 (e.g. desktop, laptop, tablet) associated with the treating physician that is communicatively coupled to a Medical Facility Computing System 205. Computing Device 210 includes a User Input 201 for receiving data or commands from a user, for example input sample results or a request to initiate a differential diagnostic session according to any of the methods described herein. Computing Device 210 includes a Processor 202 coupled to a System Memory 204, a Communication Interface 206 and an Output Module 210 that is coupled to a User Interface 212. Communication Interface 206 is communicatively coupled to a Network Server 207 of the Medical Facility System 205, which includes a computing system a Comparison Engine 209, such as described previously. In one aspect, since the Comparison Engine 209 is coupled with the Network Server 207 of Medical Facility System 205, the Comparison Engine 209 can determine a differential relationship between the first and second sets of values without the need to send those particular values to Computing Device 210. Typically, the first and second sets of values are received as Laboratory Sample Result Data 203 sent from a laboratory associated with the Medical Facility System 205. In such an embodiment, the Computing Device 210 initiates the diagnostic method by a communication request to the Medical Facility System 205, which can then determine (or obtain from yet another system), a differential relationship between the first values corresponding to a baseline cortisol/ACTH ratio and the second set of values corresponding to the GRA-exposed cortisol/ACTH ratio. The result of the differential relationship can be communicated back to Computing Device 210, which can output a differential diagnosis indication on User Interface 212 based on the differential relationship, as described above.

Figure 3:
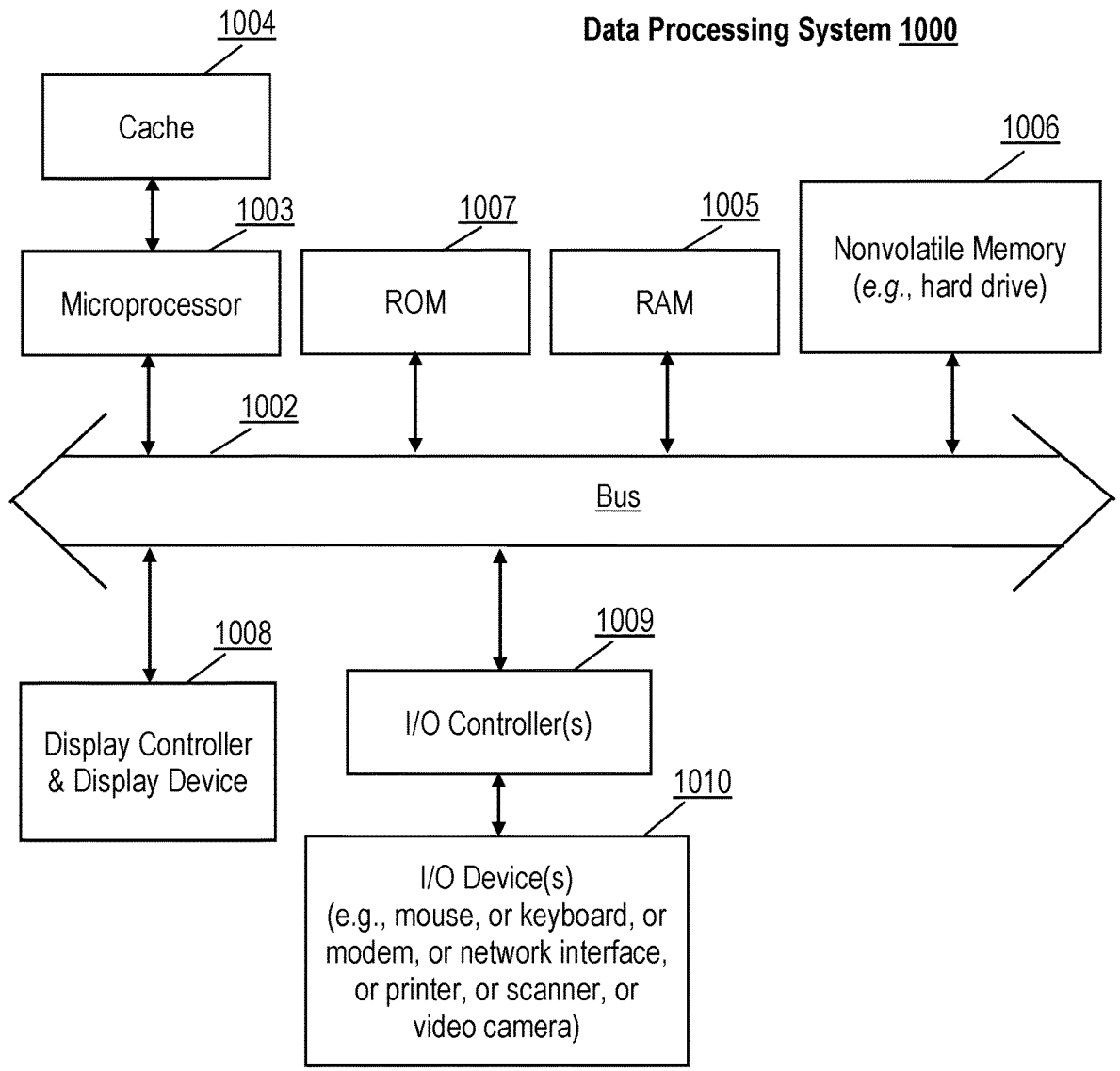
FIG. 3 shows a data processing system adapted for use in systems alternative system adapted for differentially diagnosing Cushing's Disease from Ectopic Cushing's Syndrome in accordance with various embodiments.

FIG. 3 depicts an example block diagram of a data processing system upon which the disclosed embodiments may be implemented. Embodiments of the present invention may be practiced with various computer system configurations such as hand-held devices, microprocessor systems, microprocessor-based or programmable user electronics, minicomputers, mainframe computers and the like. The embodiments can also be practiced in distributed computing environments where tasks are performed by remote processing devices that are linked through a wire-based or wireless network or remotely through a cloud server.

An example of a data processing system is shown in FIG. 3, which depicts a Data Processing System 1000 that can be used with the embodiments described herein. Note that while various components of a data processing system are depicted, it is not intended to represent any particular architecture or manner of interconnecting the components as such details are not germane to the techniques described herein. It will also be appreciated that network computers and other data processing systems which have fewer components or perhaps more components may also be used. For example, the data processing system could be distributed across multiple computing devices that are communicatively coupled. The data processing system of FIG. 3 can be a personal computer (PC), workstation, tablet, smartphone or other hand-held wireless device, or any device having similar functionality.

As shown, the data processing system 1000 includes a system bus 1002 which is coupled to a microprocessor 1003, a Read-Only Memory (ROM) 1007, a volatile Random Access Memory (RAM) 1005, as well as other nonvolatile memory 1006. In the illustrated embodiment, microprocessor 1003 is coupled to cache memory 1004. System bus 1002 can be adapted to interconnect these various components together and also interconnect components 1003, 1007, 1005, and 1006 to a display controller and display device 1008, and to peripheral devices such as input/output ("I/O") devices 1010. Types of I/O devices can include keyboards, modems, network interfaces, printers, scanners, video cameras, or other devices well known in the art. Typically, I/O devices 1010 are coupled to the system bus 1002 through I/O controllers 1009. In one embodiment the I/O controller 1009 includes a Universal Serial Bus ("USB") adapter for controlling USB peripherals or other type of bus adapter.

RANI 1005 can be implemented as dynamic RANI ("DRAM") which requires power continually in order to refresh or maintain the data in the memory. The other nonvolatile memory 1006 can be a magnetic hard drive, magnetic optical drive, optical drive, DVD RAM, or other type of memory system that maintains data after power is removed from the system. While nonvolatile memory 1006 is shown as a local device coupled with the rest of the components in the data processing system, it will be appreciated that the described techniques can use a nonvolatile memory remote from the system, such as a network storage device coupled with the data processing system through a network interface such as a modem or Ethernet interface (not shown).

With these embodiments in mind, it will be apparent from this description that aspects of the described techniques may be embodied, at least in part, in software, hardware, firmware, or any combination thereof. It should also be understood that embodiments can employ various computer-implemented functions involving data stored in a data processing system. That is, the techniques may be carried out in a computer or other data processing system in response executing sequences of instructions stored in memory. In various embodiments, hardwired circuitry may be used independently, or in combination with software instructions, to implement these techniques. For instance, the described functionality may be performed by specific hardware components containing hardwired logic for performing operations, or by any combination of custom hardware components and programmed computer components. The techniques described herein are not limited to any specific combination of hardware circuitry and software.

Embodiments herein may also be in the form of computer code stored on a computer-readable storage medium embodied in computer hardware or a computer program product. Computer-readable media can be adapted to store computer program code, which when executed by a computer or other data processing system, such as data processing system 1000, is adapted to cause the system to perform operations according to the techniques described herein. Computer-readable media can include any mechanism that stores information in a form accessible by a data processing device such as a computer, network device, tablet, smartphone, or any device having similar functionality. Examples of computer-readable media include any type of tangible article of manufacture capable of storing information thereon such as a hard drive, floppy disk, DVD, CD-ROM, magnetic-optical disk, ROM, RAM, EPROM, EEPROM, flash memory and equivalents thereto, a magnetic or optical card, or any type of media suitable for storing electronic data. Computer-readable media can also be distributed over a network-coupled computer system, which can be stored or executed in a distributed fashion.

Figure 4:
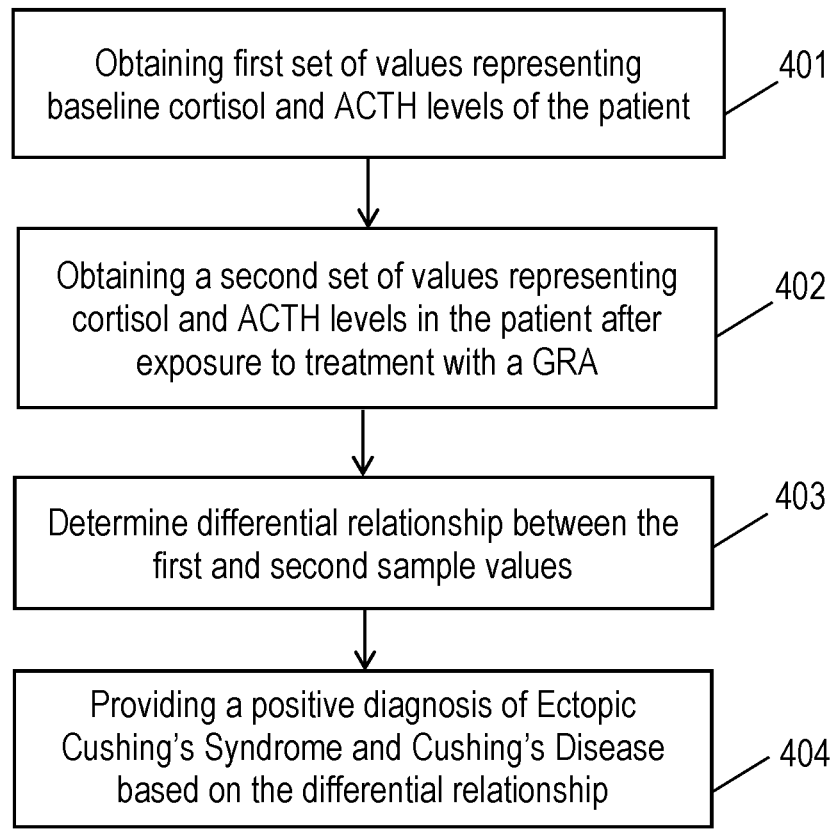
FIGS. 4-5 illustrate methods of differentially diagnosing Cushing's Disease from Ectopic Cushing's Syndrome in accordance with various embodiments

FIG. 4 shows an exemplary method of differentially diagnosing of Ectopic Cushing's Syndrome. The method includes steps of: obtaining first set of values representing baseline cortisol and ACTH levels of the patient 401 and obtaining a second set of values representing cortisol and ACTH levels in the patient after exposure to treatment with a GRA 402. Typically, the treatment includes administration of GRA to the patient for a minimum of 5 weeks in an amount effective to raise cortisol levels in a healthy person by at least two fold. It is appreciated that, in some embodiments, treatment protocols can vary. Next, a differential relationship between the first and second values is determined 403. Typically, determining a differential relationship includes determining a baseline ratio of cortisol to ACTH is determined from the first set of values, determining a GRA-exposed ratio of cortisol to ACTH is determined from the second set of values and determining a difference between baseline and GRA-exposed ratio as compared to the baseline ratio. For example, the relationship can be expressed as a percentage of increase or decrease as compared to the baseline ratio. Lastly, the method includes providing a positive diagnosis of Ectopic Cushing's Syndrome or Cushing's Disease based on the differential relationship 404. For example, a positive diagnosis for Ectopic Cushing's Syndrome is provided if the GRA-exposed ratio of cortisol to ACTH is increased by greater than 50% as compared to the baseline ratio, while a positive diagnosis for Cushing's Disease is provided if the GRA-exposed ratio of cortisol to ACTH is decreased by greater than 50% as compared to the baseline ratio. It is appreciated that the above described method can be performed, in part or in full, by use of a computing system configured to automatically perform part of all of the above steps.

Figure 5:
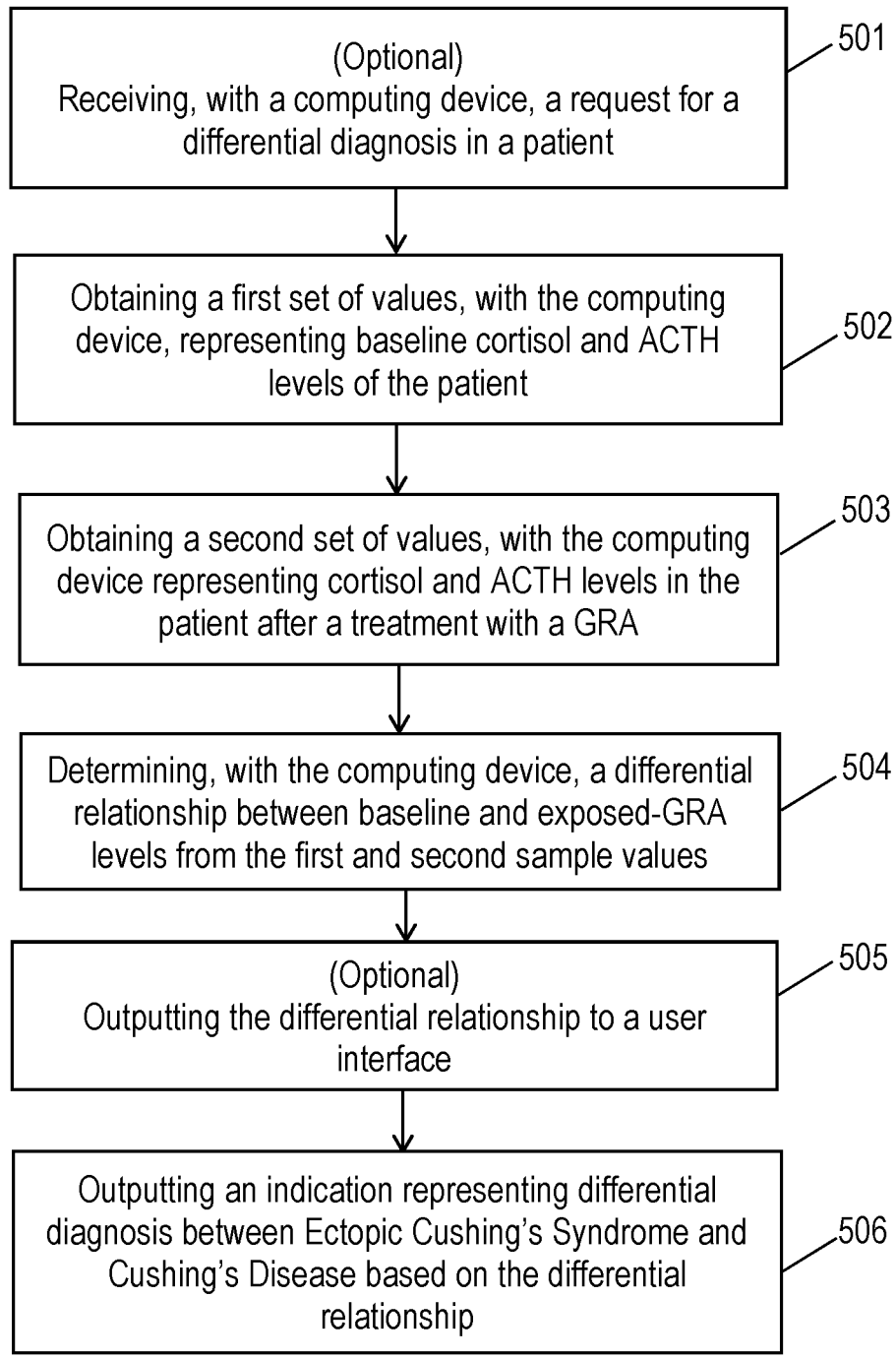

FIG. 5 shows another exemplary method of differentially diagnosing Ectopic Cushing's Syndrome by use of a computing system adapted for performing such a diagnosis. It is appreciated that the computing system can include one or more computing devices that can be communicatively coupled with a network or server. Such a method optionally includes a step of receiving, with a computing device, a request for differential diagnosis in a patient 501. Typically, such a request would be made by a treating physician for a patient that has been previously identified as suffering from hypercortisolemia and would be input through a user interface coupled with the computing device. In other embodiments, the differential diagnostic method can be performed automatically for such a patient without requiring a request from the treating physician or other personnel. The method further includes a steps of: obtaining a first set of values, with the computing device, representing baseline cortisol and ACTH levels of the patient 502 and obtaining a second set of values, with the computing device representing cortisol and ACTH levels in the patient after exposure to treatment with a GRA 503. Obtaining the first and second sets of values can include receiving an input or can include accessing the first and second sets of values from an external device or a network server communicatively coupled with the computing device. The first set of values can include values corresponding to a baseline cortisol level and a baseline ACTH level or a baseline ratio of baseline cortisol and ACTH levels. Likewise, the second set of values can include values corresponding to a GRA-exposed cortisol level and ACTH level or a GRA-exposed ratio of GRA-exposed cortisol and ACTH levels of the patient after treatment with a GRA, as described herein. The method then determines, with the computing device, a differential relationship between the first and second sample values 504, for example, as described in any of the embodiments herein. Optionally, the computing device can output, to a user, the particulars of the determined differential relationship 505 (e.g. the percentage change in the GRA-exposed ratio as compared to the baseline ratio, specific changes in cortisol or ACTH, or actual detected levels of cortisol or ACTH). The method can further include outputting an indication representing differential diagnosis between Ectopic Cushing's Syndrome and Cushing's Disease based on the differential relationship 506. Outputting the indication can include outputting a text message on a user interface display of the device itself (e.g. screen of portable computing device, monitor of a laptop or desktop) or can include outputting an indication to an external device, such as a remote computer or printer. In some embodiments, the computing device includes a processor coupled with a tangible, non-transitory memory having programmable instructions recorded thereon that cause the processor to perform any or all of the above described steps.

It should be appreciated that the specific operations illustrated in FIG. 5 depict a particular embodiment of a process and that other sequences of operations may also be performed in alternative embodiments. For example, certain steps can be performed by another computing device communicatively coupled with the computing device or the above operations could be performed in a different order. Moreover, the individual operations may include multiple sub-steps that may be performed in various sequences as appropriate and additional operations may be added or removed depending on the particular applications. One of ordinary skill in the art would recognize the many possible variations, modifications, and alternatives.

V. Examples

Example 1

Differential Diagnosis Based on the C:A Ratio

Two groups of patients, which have been previously diagnosed as having Cushing's Disease, Ectopic Cushing's Syndrome using other methods, were enrolled in the study. The investigators were blind to the patients' diagnoses.

Blood samples were obtained from each patient within 6 weeks prior to the enrollment in the study ("Day 1" samples). The patients were treated with mifepristone at a starting dose 300 mg daily, increased up to 1200 mg or 20 mg/kg over a period of 10 weeks. The mifepristone treatment continued for a total period of 24 weeks. Blood samples were taken during the course of the treatment, i.e., at the end of 14 days, and 6, 10, 16 and 24 weeks from the initial dose of mifepristone was given. All samples were taken at between 8-10 am on the day of the study.

The ACTH levels and the cortisol levels of the plasma produced from the blood samples collected above were assayed using two-site immunometric assays (Mayo Clinic, Test ID ACTH) following the manufacturer's instructions. Ratios of cortisol to ACTH were determined for each patient and the mean values of the ratios of patients in each group are shown in the table below

|   | Diagnosis | Day 1 | Day 14 | Week 6 | Week 10 | Week 16 | Week 24/ET |
|---|---|---|---|---|---|---|---|
| 1 | CD (n = 43) | 3.018 (n = 41) | — | 3.396 (n = 38) | 6.852 (n = 33) | 5.788 (n = 32) | 4.999 (n = 38) |
| 2 | Ectopic (n = 4) | 18.552 (n = 3) | — | 9.241 (n = 3) | 6.722 (n = 3) | 0.600 (n = 3) | 2.154 (n = 3) |

Note:
n is the number of patients from whom cortisol and ACTH levels and the cortisol to ACTH ratios were determined. The means of the ratios from the number of patients are reported in the table.

The results show that for patients having Cushing's Disease, the mean GRA-exposed C:A ratio increased following the mifepristone treatment and peaked at the end of 10 weeks, reaching a value more than 2 fold of the mean baseline C:A ratio. For patients having Ectopic Cushing's Syndrome, the mean GRA-exposed C:A ratio decreased to less than 50% of the mean baseline ratio at the end of the six weeks' treatment and reached a nadir at the end of 16 weeks—less than 0.02% of the mean baseline ratio. The mean GRA-exposed C:A ratio was 11.6% of the baseline ratio at the end of 24 weeks treatment.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of concurrently ) controlling hyperglycemia secondary to hypercortisolemia in a patient suffering from ACTH-dependent Cushing's syndrome and 2) differentially diagnosing Cushing's Disease from Ectopic Cushing's Syndrome in said patient, the method comprising:
Selecting a patient identified as suffering from Cushing's syndrome based on the results of a dexamethasone suppression test (DST);
(i) taking one or more pretreatment samples from the patient in order to determine a baseline cortisol level and a baseline adrenocorticotropic hormone (ACTH) level; (ii) administering a glucocorticoid receptor antagonist (GRA) to the patient; (iii) continuing said administration of said GRA to the patient for a period of not less than 5 weeks; (iv) taking one or more GRA-exposed samples from said patient in order to determine a GRA-exposed ACTH level and a GRA-exposed cortisol level; (v) calculating a baseline ratio of cortisol to ACTH ("baseline C:A ratio") using the baseline levels of cortisol and ACTH, and calculating a GRA-exposed ratio of cortisol to ACTH ("GRA-exposed C:A ratio") using the GRA-exposed cortisol level and the GRA-exposed ACTH level; and, (vi) diagnosing the patient as having Ectopic Cushing's Syndrome if the GRA-exposed C:A ratio is lower than the baseline C:A ratio, or diagnosing the patient as a having Cushing's Disease if the GRA-exposed C:A ratio is higher than the baseline C:A ratio.

2. The method of claim 1, comprising diagnosing the patient as having Ectopic Cushing's Syndrome if the GRA-exposed C:A ratio is lower than the baseline C:A ratio by at least 50% of the baseline C:A ratio, or diagnosing the patient as a having Cushing's Disease if the GRA-exposed C:A ratio is higher than the baseline C:A ratio than the baseline C:A ratio by at least 20% of the baseline C:A ratio.

3. The method of claim 1, wherein the GRA is mifepristone, and the one or more GRA-exposed samples are taken from the patient after mifepristone has been administered for a minimum of 6 weeks and on a daily basis at a dosage that does not exceed 1200 mg/day.

4. The method of claim 1, wherein the GRA is a non-steroidal GRA, and the GRA-exposed ACTH and GRA-exposed cortisol levels are determined after administration of said GRA for a minimum of 6 weeks.

5. The method of claim 1, where the one or more pretreatment samples and the one or more GRA-exposed samples are from saliva, and wherein said GRA-exposed ACTH and cortisol levels are i) determined from a first GRA-exposed saliva sample after administration of said GRA for a period of between 6 and 10 weeks, and ii) are determined from at least one further GRA-exposed saliva sample obtained after administration of the GRA for at least a further 4 weeks after said first GRA-exposed saliva sample was obtained.

6. The method of claim 1 where the one or more pretreatment samples and the one or more GRA-exposed samples are from plasma, and wherein said GRA-exposed ACTH and cortisol levels are i) determined from a first GRA-exposed plasma sample after administration of said GRA for a period of between 6 and 10 weeks, and ii) are determined from at least one further GRA-exposed plasma sample obtained after administration of the GRA for at least a further 4 weeks after said first GRA-exposed plasma sample was obtained.

7. The method of claim 1 where the one or more pretreatment samples and the one or more GRA-exposed samples are from 24-hour urine collections, and wherein said GRA-exposed ACTH and cortisol levels are i) determined from a first GRA-exposed 24-hour urine collection sample after administration of said GRA for a period of between 6 and 10 weeks, and ii) are determined from at least one further GRA-exposed 24-hour urine collection sample obtained after administration of the GRA for at least a further 4 weeks after said first GRA-exposed 24-hour urine collection sample was obtained.

8. A method of concurrently 1) controlling hyperglycemia secondary to hypercortisolemia in a patient suffering from endogenous ACTH-dependent Cushing's syndrome and 2) differentially diagnosing Cushing's Disease from Ectopic Cushing's Syndrome in said patient, the method comprising:
taking one or more pretreatment samples from said patient in order to determine a baseline cortisol level and a baseline adrenocorticotropic hormone (ACTH) level;
obtaining, with a computing system associated with a treating physician, a first set of values representing said baseline cortisol level and said baseline ACTH level, or a baseline C:A ratio, wherein said baseline C:A ratio is a ratio between the baseline cortisol and baseline ACTH levels determined from said one or more pretreatment samples from the patient; then administering a glucocorticoid receptor antagonist (GRA) to the patient; then taking one or more GRA-exposed samples from said patient in order to determine a GRA-exposed cortisol level and a GRA-exposed ACTH level;

obtaining, with the computing system, a second set of values representing said GRA-exposed cortisol level and said GRA-exposed ACTH level, or a GRA-exposed C:A ratio, wherein said GRA-exposed C:A ratio is a ratio between the GRA-exposed cortisol and GRA-exposed ACTH levels corresponding to the one or more GRA-exposed samples from the patient obtained after GRA administration; determining, with the computing system, a differential relationship between the first and second set of values; and outputting to a user, with the computing system, an indication representing a positive diagnosis for Ectopic Cushing's Syndrome, if the differential relationship represents or exceeds a pre-determined decrease of the GRA-exposed levels as compared to the baseline levels; and outputting to a user, with the computing system, an indication representing a positive diagnosis for Cushing's Disease, if the differential relationship represents or exceeds a pre-determined increase of the GRA-exposed levels as compared to the baseline levels.

9. The method of claim 8, wherein the pre-determined treatment protocol includes administration of said GRA to the patient for a minimum of five weeks, wherein the GRA is mifepristone, and said mifepristone is administered on a daily basis at a dosage that does not exceed 1200 mg/day.

10. The method of claim 8, wherein said pre-determined decrease is 50%, and an indication representing a positive diagnosis for Ectopic Cushing's Syndrome is output if the GRA-exposed C:A ratio is lower than the baseline C:A ratio by at least 50% of the baseline C:A ratio.

11. The method of claim 8, wherein the pre-determined increase is 20%, and an indication representing a positive diagnosis for Cushing's Disease is output if the GRA-exposed C:A ratio is higher than the baseline C:A ratio by at least 20% of the baseline C:A ratio.

12. The method of claim 8, wherein the GRA is a non-steroidal GRA, and the GRA-exposed ACTH and GRA-exposed cortisol levels are determined after administration of said GRA for a minimum of 6 weeks.

13. The method of claim 8, wherein obtaining the first set of values comprises storing, in a memory of the computing system, the first set of values designated as corresponding to baseline levels of the patient and obtaining the second set of values comprises storing the second set of values, in the memory, designated as corresponding to GRA-exposed levels of the patient.

14. The method of claim 8, wherein obtaining the first and second sets of values comprises accessing the first and second sets of values remotely through a server of a medical facility or laboratory associated with the patient.

15. The method of claim 8, wherein the pre-determined decrease is 50% of the baseline C:A ratio and the pre-determined increase is 20% of the baseline C:A ratio.

16. A method of concurrently 1) controlling hyperglycemia secondary to hypercortisolemia in a patient suffering from ACTH-dependent Cushing's syndrome and 2) differentially diagnosing Cushing's Disease from Ectopic Cushing's Syndrome in said patient, the method comprising:

Selecting a patient identified as suffering from Cushing's syndrome based on the results of a measurement of the patient's cortisol level by 24-hour urinary free cortisol measurement (UFC), salivary cortisol, or both;

(i) determining a baseline cortisol level and a baseline adrenocorticotropic hormone (ACTH) level prior to administering a glucocorticoid receptor antagonist (GRA); (ii) administering a GRA to the patient; (iii) continuing said administration of said GRA to the patient for a period of not less than 5 weeks; (iv) taking one or more GRA-exposed samples from the patient in order to determine a GRA-exposed cortisol level and a GRA-exposed ACTH level;

(v) calculating a baseline ratio of cortisol to ACTH ("baseline C:A ratio") using the baseline levels of cortisol and ACTH, and calculating a GRA-exposed ratio of cortisol to ACTH ("GRA-exposed C:A ratio") using the GRA-exposed cortisol and GRA-exposed ACTH levels; and, (vi) diagnosing the patient as having Ectopic Cushing's Syndrome if the GRA-exposed C:A ratio is lower than the baseline C:A ratio, or diagnosing the patient as having Cushing's Disease if the GRA-exposed C:A ratio is higher than the baseline C:A ratio.

17. The method of claim 16, comprising diagnosing the patient as having Ectopic Cushing's Syndrome if the GRA-exposed C:A ratio is lower than the baseline C:A ratio by at least 50% of the baseline C:A ratio, or diagnosing the patient as a having Cushing's Disease if the GRA-exposed C:A ratio is higher than the baseline C:A ratio by at least 20% of the baseline C:A ratio.

18. The method of claim 16, wherein the GRA is mifepristone, and the one or more GRA-exposed samples are taken from the patient after mifepristone has been administered for a minimum of 6 weeks and on a daily basis at a dosage that does not exceed 1200 mg/day.

19. The method of claim 16, wherein the GRA is a non-steroidal GRA, and the GRA-exposed ACTH and GRA-exposed cortisol levels are determined after administration of said GRA for a minimum of 6 weeks.

20. The method of claim 16 where the one or more GRA-exposed samples are from saliva, and wherein said GRA- exposed ACTH and cortisol levels are i) determined from a first GRA-exposed saliva sample after administration of said GRA for a period of between 6 and 10 weeks, and ii) are determined from at least one further GRA-exposed saliva sample obtained after administration of the GRA for at least a further 4 weeks after said first GRA-exposed saliva sample was obtained.

21. The method of claim 16 where the one or more GRA-exposed samples are from 24-hour urine collections, and wherein said GRA-exposed ACTH and cortisol levels are i) determined from a first GRA-exposed 24-hour urine collection sample after administration of said GRA for a period of between 6 and 10 weeks, and ii) are determined from at least one further GRA-exposed 24-hour urine collection sample obtained after administration of the GRA for at least a further 4 weeks after said first GRA-exposed 24-hour urine collection sample was obtained.

22. The method of claim 16 where the one or more GRA-exposed samples are from plasma, and wherein said GRA- exposed ACTH and cortisol levels are i) determined from a first GRA-exposed plasma sample after administration of said GRA for a period of between 6 and 10 weeks, and ii) are determined from at least one further GRA-exposed plasma sample obtained after administration of the GRA for at least a further 4 weeks after said first GRA-exposed plasma sample was obtained.

23. A method of concurrently treating 1) controlling hyperglycemia secondary to hypercortisolemia in a patient suffering from ACTH-dependent Cushing's syndrome and 2) differentially diagnosing Cushing's Disease from Ectopic Cushing's Syndrome in said patient, the method comprising:

Selecting a patient identified as suffering from Cushing's syndrome based on the results of a measurement of the patient's cortisol level by 24-hour urinary free cortisol measurement (UFC), salivary cortisol, or both;
obtaining, with a computing system associated with a treating physician, a first set of values representing a baseline cortisol level and a baseline ACTH level, or a baseline C:A ratio, wherein said baseline C:A ratio is a ratio between the baseline cortisol and baseline ACTH levels determined from said one or more pre-treatment samples from the patient; then administering a glucocorticoid receptor antagonist (GRA) to the patient; then obtaining, with the computing system, a second set of values representing a GRA-exposed cortisol level and a GRA-exposed ACTH level, or a GRA-exposed C:A ratio, wherein said GRA-exposed C:A ratio is a ratio between the GRA-exposed cortisol and GRA-exposed ACTH levels determined from said one or more GRA-exposed samples obtained from the patient after GRA administration; determining, with the computing system, a differential relationship between the first and second set of values;
and outputting to a user, with the computing system, an indication representing a positive diagnosis for Ectopic Cushing's Syndrome, if the differential relationship represents or exceeds a pre-determined decrease of the exposed-GRA levels as compared to the baseline levels; and
outputting to a user, with the computing system, an indication representing a positive diagnosis for Cushing's Disease, if the differential relationship represents or exceeds a pre-determined increase of the exposed-GRA levels as compared to the baseline levels.

24. The method of claim 23, wherein the pre-determined treatment protocol includes administration of said GRA to the patient for a minimum of five weeks, wherein the GRA is mifepristone, and said mifepristone is administered on a daily basis at a dosage that does not exceed 1200 mg/day.

25. The method of claim 23, wherein the pre-determined decrease is 50%, and an indication representing a positive diagnosis for Ectopic Cushing's Syndrome is output if the GRA-exposed C:A ratio is lower than the baseline C:A ratio by more than 50% of the baseline C:A ratio.

26. The method of claim 23, wherein the pre-determined increase is 20%, and an indication representing a positive diagnosis for Cushing's Disease is output if the GRA-exposed C:A ratio is higher than the baseline C:A ratio by more than 20% of the baseline C:A ratio.

27. The method of claim 23, wherein the GRA is a non-steroidal GRA, and the GRA-exposed ACTH and GRA-exposed cortisol levels are determined after administration of said GRA for a minimum of 6 weeks.

28. The method of claim 23, wherein obtaining the first set of values comprises storing, in a memory of the computing system, the first set of values designated as corresponding to baseline levels of the patient and obtaining the second set of values comprises storing the second set of values, in the memory, designated as corresponding to GRA-exposed levels of the patient.

29. The method of claim 23, wherein the pre-determined decrease is 50% of the baseline C:A ratio and the pre-determined increase is 20% of the baseline C:A ratio.

* * * * *

UNITED STATES PATENT AND TRADEMARK OFFICE
CERTIFICATE OF CORRECTION

PATENT NO. : 11,327,083 B2
APPLICATION NO. : 16/158866
DATED : May 10, 2022
INVENTOR(S) : Andreas G. Moraitis Page 1 of 1

It is certified that error appears in the above-identified patent and that said Letters Patent is hereby corrected as shown below:

In the Claims

Column 37, Line 50, Claim 1: please delete "concurrently )" and insert --concurrently 1)--.

Signed and Sealed this
Twenty-ninth Day of October, 2024

Katherine Kelly Vidal
*Director of the United States Patent and Trademark Office*